US010584374B2

(12) United States Patent
Rawlings et al.

(10) Patent No.: US 10,584,374 B2
(45) Date of Patent: Mar. 10, 2020

(54) METHODS, CARRIER ASSEMBLIES, AND SYSTEMS FOR IMAGING SAMPLES FOR BIOLOGICAL OR CHEMICAL ANALYSIS

(71) Applicant: Illumina Cambridge Limited, Essex (GB)

(72) Inventors: Stephen Rawlings, Essex (GB); Venkatesh Mysore Nagaraja Rao, Singapore (SG); Beng Keong Ang, Singapore (SG); Nitin Udpa, San Diego, CA (US)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 44 days.

(21) Appl. No.: 15/967,555

(22) Filed: Apr. 30, 2018

(65) Prior Publication Data
US 2018/0245143 A1 Aug. 30, 2018

Related U.S. Application Data

(62) Division of application No. 15/077,182, filed on Mar. 22, 2016, now Pat. No. 9,976,174.

(60) Provisional application No. 62/137,600, filed on Mar. 24, 2015.

(51) Int. Cl.
| | | |
|---|---|---|
| *C12Q 1/6837* | (2018.01) | |
| *G01N 21/13* | (2006.01) | |
| *G01N 21/25* | (2006.01) | |
| *G01N 21/64* | (2006.01) | |
| *G02B 21/34* | (2006.01) | |
| *G01N 35/10* | (2006.01) | |
| *B01L 9/00* | (2006.01) | |
| *C12Q 1/6869* | (2018.01) | |
| *G01N 35/00* | (2006.01) | |
| *B01L 3/00* | (2006.01) | |
| *B01L 7/00* | (2006.01) | |
| *G01N 35/04* | (2006.01) | |

(52) U.S. Cl.
CPC ............ *C12Q 1/6837* (2013.01); *B01L 9/527* (2013.01); *C12Q 1/6869* (2013.01); *G01N 21/13* (2013.01); *G01N 21/253* (2013.01); *G01N 21/6452* (2013.01); *G01N 35/1095* (2013.01); *G02B 21/34* (2013.01); *B01L 3/5027* (2013.01); *B01L 7/52* (2013.01); *B01L 9/52* (2013.01); *B01L 2300/0654* (2013.01); *B01L 2300/0816* (2013.01); *B01L 2300/0822* (2013.01); *B01L 2300/0877* (2013.01); *G01N 35/04* (2013.01); *G01N 2035/0091* (2013.01); *G01N 2035/00356* (2013.01); *G01N 2035/00752* (2013.01); *G01N 2201/025* (2013.01)

(58) Field of Classification Search
CPC .... C12Q 1/6837; G01N 35/1095; B01L 9/527
See application file for complete search history.

(56) References Cited

U.S. PATENT DOCUMENTS

| | | |
|---|---|---|
| 5,324,633 A | 6/1994 | Fodor et al. |
| 5,451,683 A | 9/1995 | Barrett et al. |
| 5,482,867 A | 1/1996 | Barrett et al. |
| 5,491,074 A | 2/1996 | Aldwin et al. |
| 5,624,711 A | 4/1997 | Sundberg et al. |
| 5,641,658 A | 6/1997 | Adams et al. |
| 5,744,305 A | 4/1998 | Fodor et al. |
| 5,795,716 A | 8/1998 | Chee et al. |
| 5,831,070 A | 11/1998 | Pease et al. |
| 5,856,101 A | 1/1999 | Hubbell |
| 5,858,659 A | 1/1999 | Sapolsky et al. |
| 5,874,219 A | 2/1999 | Rava et al. |
| 5,968,740 A | 10/1999 | Fodor et al. |
| 5,974,164 A | 10/1999 | Chee et al. |
| 5,981,185 A | 11/1999 | Matson et al. |
| 5,981,956 A | 11/1999 | Stern |
| 6,022,963 A | 2/2000 | McGall et al. |
| 6,025,601 A | 2/2000 | Trulson et al. |
| 6,033,860 A | 3/2000 | Lockhart et al. |
| 6,083,697 A | 7/2000 | Beecher et al. |

(Continued)

FOREIGN PATENT DOCUMENTS

| | | |
|---|---|---|
| CN | 1875261 | 12/2006 |
| JP | 2006145393 | 6/2006 |

(Continued)

OTHER PUBLICATIONS

PCT/US2016/023565, International Preliminary Report on Patentability and Written Opinion of the International Searching Authority, dated Sep. 26, 2017.
PCT/US2016/023565, International Search Report and Written Opinion, dated Aug. 18, 2016.
Bentley, et al., "Accurate whole human genome sequencing using reversible terminator chemistry", Nature, vol. 456, Nov. 6, 2008, 53-59.
Cockroft, et al., "A single-molecule nanpore device detects DNA polymerase activity with single-nucleotide resolution", J. Am. Chem. Soc, 130(3), Jan. 23, 2008, 818-820.

(Continued)

*Primary Examiner* — Narayan K Bhat
(74) *Attorney, Agent, or Firm* — Illumina, Inc.

(57) ABSTRACT

Method includes positioning a first carrier assembly on a system stage. The carrier assembly includes a support frame having an inner frame edge that defines a window of the support frame. The first carrier assembly includes a first substrate that is positioned within the window and surrounded by the inner frame edge. The first substrate has a sample thereon. The method includes detecting optical signals from the sample of the first substrate. The method also includes replacing the first carrier assembly on the system stage with a second carrier assembly on the system stage. The second carrier assembly includes the support frame and an adapter plate held by the support frame. The second carrier assembly has a second substrate held by the adapter plate that has a sample thereon. The method also includes detecting optical signals from the sample of the second substrate.

20 Claims, 15 Drawing Sheets

(56) References Cited

U.S. PATENT DOCUMENTS

| | | |
|---|---|---|
| 6,090,555 A | 7/2000 | Fiekowsky et al. |
| 6,136,269 A | 10/2000 | Winkler et al. |
| 6,210,891 B1 | 4/2001 | Nyren et al. |
| 6,258,568 B1 | 7/2001 | Nyren |
| 6,266,459 B1 | 7/2001 | Walt et al. |
| 6,274,320 B1 | 8/2001 | Rothberg et al. |
| 6,291,183 B1 | 9/2001 | Pirrung et al. |
| 6,309,831 B1 | 10/2001 | Goldberg |
| 6,355,431 B1 | 3/2002 | Chee et al. |
| 6,416,949 B1 | 7/2002 | Dower et al. |
| 6,428,752 B1 | 8/2002 | Montagu |
| 6,482,591 B2 | 11/2002 | Lockhart et al. |
| 6,770,441 B2 | 8/2004 | Dickinson et al. |
| 6,859,570 B2 | 2/2005 | Walt et al. |
| 7,001,792 B2 | 2/2006 | Sauer et al. |
| 7,057,206 B2 | 6/2006 | Halik et al. |
| 7,106,513 B2 | 9/2006 | Moon et al. |
| 7,115,400 B1 | 10/2006 | Adessi et al. |
| 7,164,533 B2 | 1/2007 | Moon et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,329,860 B2 | 2/2008 | Feng et al. |
| 7,399,643 B2 | 7/2008 | Moon |
| 7,405,281 B2 | 7/2008 | Xu et al. |
| 7,622,294 B2 | 11/2009 | Walt et al. |
| 7,769,548 B2 | 8/2010 | Garcia |
| 8,481,903 B2 | 7/2013 | Triener et al. |
| 8,748,789 B2 | 6/2014 | Triener et al. |
| 8,951,781 B2 | 2/2015 | Reed et al. |
| 2002/0005510 A1 | 5/2002 | Kawashima et al. |
| 2003/0010886 A1 | 6/2003 | Chee et al. |
| 2003/0010890 A1 | 6/2003 | Oliphant et al. |
| 2003/0017068 A1 | 9/2003 | Fan |
| 2003/0020729 A1 | 11/2003 | Gunderson et al. |
| 2004/0000209 A1 | 1/2004 | Mayer et al. |
| 2004/0009685 A1 | 5/2004 | Mayer |
| 2005/0004264 A1 | 2/2005 | Griffiths et al. |
| 2005/0007951 A1 | 4/2005 | Berka et al. |
| 2005/0013017 A1 | 6/2005 | Leamon et al. |
| 2005/0018139 A1 | 8/2005 | Steemers et al. |
| 2005/0022725 A1 | 10/2005 | Moon et al. |
| 2007/0099208 A1 | 5/2007 | Drmanac et al. |
| 2007/0012862 A1 | 6/2007 | Gormley et al. |
| 2008/0000942 A1 | 1/2008 | Schroth et al. |
| 2008/0010808 A1 | 5/2008 | Rank et al. |
| 2008/0028152 A1 | 11/2008 | Garcia |
| 2008/0281527 A1 | 11/2008 | Garcia et al. |
| 2009/0002361 A1 | 1/2009 | Peytavi et al. |
| 2009/0027291 A1 | 11/2009 | Feng et al. |
| 2010/0008732 A1 | 4/2010 | Buermann |
| 2010/0015708 A1 | 6/2010 | Segale et al. |
| 2011/0022077 A1 | 9/2011 | Triener et al. |
| 2011/0220775 A1 | 9/2011 | Triener et al. |
| 2012/0270305 A1 | 10/2012 | Reed et al. |
| 2013/0026037 A1 | 10/2013 | Buermann et al. |

FOREIGN PATENT DOCUMENTS

| | | |
|---|---|---|
| JP | 2007093443 | 4/2007 |
| JP | 2014228411 | 12/2014 |
| JP | 2015514218 | 5/2015 |
| WO | 1991/006678 A1 | 5/1991 |
| WO | 1998/059066 A1 | 12/1998 |
| WO | 2000/063437 A2 | 10/2000 |
| WO | 2004/018497 A2 | 3/2004 |
| WO | 2004/024328 A1 | 3/2004 |
| WO | 2005/010145 A2 | 2/2005 |
| WO | 2005/033681 A1 | 4/2005 |
| WO | 2005/045402 | 5/2005 |
| WO | 2006/076053 A1 | 7/2006 |
| WO | 2007/123744 A2 | 11/2007 |
| WO | 2009/042862 A1 | 4/2009 |
| WO | 2009/137435 A1 | 11/2009 |
| WO | 2013151622 | 10/2013 |

OTHER PUBLICATIONS

Deamer, et al., "Characterization of nucleic acids by nanopore analysis", ACC Chem Res, 35(10), 2002, 817-825.

Dressman, et al., "Transforming single DNA molecules into fluorescent magnetic particles for detection and enumeration of genetic variations", PNAS, 100(15), 2003, 8817-8822.

Haugland, "Introduction to fluorescence techniques," Molecular Probes Handbook, 2002.

Healy, K., "Nanopore-based single-molecule DNA analysis", Nanomed. 2(4), 2007, 459-481.

Lakowicz, J.R., "Principles of Fluorescent Spectroscopy, 2nd Edition.", Kluwer Academic/Plenum Publisheers: New York, NY (1999), N/A.

Li, et al., "DNA molecules and configurations in a solid-state nanopore microscope", Nature Mater, 2(9), 2003, 611-615.

Lizardi, et al. "Mutation detection and single-molecule counting using isothermal rolling-circle amplification", Nature Genetics, vol. 19, 1998, 225-232.

Ronaghi, M., "Pyrosequencing sheds light on DNA sequencing", Genome Res, 11(1), 2001, 3-11.

Soni, et al., "Progress toward Ultrafast DNA Sequencing Using Solid-State Nanopores", Clin Chem, 53(11), 2007, 1996-2001.

METHODS, CARRIER ASSEMBLIES, AND SYSTEMS FOR IMAGING SAMPLES FOR BIOLOGICAL OR CHEMICAL ANALYSIS

CROSS-REFERENCE TO RELATED APPLICATION

The present application is a divisional of U.S. patent application Ser. No. 15/077,182, filed on Mar. 22, 2016, which claims the benefit of U.S. Provisional Patent Application No. 62/137,600, filed on Mar. 24, 2015, each of which is incorporated herein by reference in its entirety.

BACKGROUND OF THE INVENTION

Embodiments of the present invention relate generally to biological or chemical analysis and more particularly, to methods, carrier assemblies, and systems for detecting optical signals from samples for biological or chemical analysis.

Various assay protocols used for biological or chemical research are concerned with performing a large number of controlled reactions. In some cases, the controlled reactions are performed on support surfaces. The designated reactions may then be observed and analyzed to help identify properties or characteristics of the chemicals involved in the designated reaction. For example, in some protocols, a chemical moiety that includes an identifiable label (e.g., fluorescent label) may selectively bind to another chemical moiety under controlled conditions. These chemical reactions may be observed by exciting the labels with radiation and detecting light emissions from the labels.

Examples of such protocols include DNA sequencing and multiplex array-based assays. In one sequencing-by-synthesis (SBS) protocol, clusters of clonal amplicons are formed through bridge PCR on a surface of a channel of a flow cell. After generating the clusters of clonal amplicons, the amplicons may be "linearized" to make single stranded DNA (sstDNA). A predetermined sequence of reagents may be flowed into the flow cell to complete a cycle of sequencing. Each sequencing cycle extends the sstDNA by a single nucleotide (e.g., A, T, G, C) having a unique fluorescent label. Each nucleotide has a reversible terminator that allows only a single-base incorporation to occur in one cycle. After nucleotides are added to the sstDNAs clusters, an image in four channels is taken (i.e., one for each fluorescent label). After imaging, the fluorescent label and the terminator are chemically cleaved from the sstDNA and the growing DNA strand is ready for another cycle. Several cycles of reagent delivery and optical detection can be repeated to determine the sequences of the nucleic acids of the clonal amplicons.

In some multiplex array-based assay protocols, populations of different probe molecules are immobilized to a substrate surface. The probes may be differentiated based on each probe's address on the substrate surface. For example, each population of probe molecules may have a known location (e.g., coordinates on a grid) on the substrate surface. The probe molecules are exposed to target analytes under controlled conditions such that a detectable change occurs at one or more addresses due to a specific interaction between a target analyte and the probe. For example, a fluorescently labeled target analyte that binds to a specific probe can be identified based on recruitment of the fluorescent label to the address of the probe. The addresses on the array can be determined by an assay system to identify which populations reacted with the analytes. By knowing the chemical structure of the probe molecules that reacted with the analytes, properties of the analyte may be determined. In other multiplex assays, designated reactions are conducted on surfaces of individually identifiable microparticles that may also be scanned and analyzed.

Different assay protocols, such as those described above, may include particular features or involve particular steps that do not occur in other assay protocols. For example, different assay protocols may use different types of reagents or reagents having unique modifications, labels with different emission spectra, different types of optical substrates for supporting the samples (e.g., flow cells, open-face substrates, microarrays, wells, microparticles), different light sources with different excitation spectra, different optical components (e.g., objective lenses), thermal conditions, and software. Furthermore, the devices typically operate at a high level of precision since detection occurs at a resolution of a few microns or less. As a result, platforms that exist today are generally concerned with performing only one type of assay protocol.

Accordingly, there is a need for assay systems and corresponding components that are capable of conducting more than one type of assay protocol.

BRIEF DESCRIPTION OF THE INVENTION

In an embodiment, a method is provided that includes positioning a first carrier assembly on a system stage. The first carrier assembly includes a support frame having an inner frame edge that defines a window of the support frame. The first carrier assembly includes a removable first substrate that is positioned within the window and surrounded by the inner frame edge. The first substrate has a sample thereon that is positioned within an imaging zone of an optical system. The method also includes detecting optical signals from the sample of the first substrate using the optical system in accordance with a first imaging protocol. The method also includes replacing the first carrier assembly with a second carrier assembly on the system stage. The second carrier assembly has a removable second substrate. The second substrate has a sample thereon that is positioned within the imaging zone of the optical system, wherein the first and second substrates are different types of substrates. The method also includes detecting optical signals from the sample of the second substrate using the optical system in accordance with a second imaging protocol that is different from the first imaging protocol. Optionally, the first imaging protocol and/or the second imaging protocol are automated.

In accordance with an embodiment, a method is provided that includes positioning a first carrier assembly on a system stage. The carrier assembly includes a support frame having an inner frame edge that defines a window of the support frame. The first carrier assembly includes a first substrate that is positioned within the window and surrounded by the inner frame edge. The first substrate has a sample thereon that is positioned within an imaging zone of an optical system. The method includes detecting optical signals from the sample of the first substrate using the optical system. The method also includes replacing the first carrier assembly on the system stage with a second carrier assembly on the system stage. The second carrier assembly includes the support frame and an adapter plate held by the support frame. The second carrier assembly has a second substrate held by the adapter plate that has a sample thereon. The sample of the second substrate is positioned within the imaging zone of an optical system. The method also includes detecting optical signals from the sample of the second substrate using the optical system.

In accordance with an embodiment, a carrier assembly is provided that includes a support frame having an inner frame edge that defines a window of the support frame and an adapter plate coupled to the support frame and positioned within the window. The adapter plate includes a plate body having an inner plate edge that defines a pocket for receiving a substrate that is sized smaller than the window. The inner plate edge also defines a holding recess that opens to the pocket. The carrier assembly also includes a movable datum block positioned within the holding recess. The datum block is movable between a retracted position and an engaged position. The datum block is configured to engage the substrate when the datum block is in the engaged position and press the substrate against an opposing surface of the adapter plate to hold the substrate within the pocket.

In accordance with an embodiment, a carrier assembly is provided that includes a support frame having an inner frame edge that defines a window of the support frame. The carrier assembly also includes an adapter plate coupled to the support frame and positioned within the window. The inner frame edge defines a substrate-receiving recess positioned above the adapter plate. The substrate-receiving recess is configured to receive a first planar substrate. The adapter plate includes a plate body having an inner plate edge that defines a pocket for receiving a second planar substrate that is sized smaller than the first planar substrate. The pocket exists at least partially below the substrate-receiving recess.

In accordance with an embodiment, an assay system is provided that includes a system stage having a base surface that extends parallel to an XY plane and a plurality of datums coupled to the base surface. The datums include projections that extend away from the base surface along a Z axis that is perpendicular to the XY plane. The assay system also includes an optical system having an objective lens. The objective lens is configured to move relative to the system stage along the XY plane. The assay system also includes a fluidic control system configured to control flow of one or more fluids through a flow cell when the flow cell is mounted onto the system stage. The assay system also includes a system controller that is configured to control the fluidic control system and the optical system to conduct different first and second assay protocols with first and second samples, respectively. During the first assay protocol, the system controller commands the fluidic control system to direct one or more fluids through the flow cell on the system stage and commands the optical system to detect optical signals from the first sample on the flow cell. During the second assay protocol, the system controller commands optical system to detect optical signals from the second sample on an open-face substrate on the system stage without flowing fluids through the second sample.

In one embodiment, a method is provided that includes capturing a series of images of overlapping portions of a microarray of features. Each of the features has designated probe molecules immobilized thereto. The microarray has target analytes attached thereto. The method also includes analyzing light intensities associated with respective features in the images to determine data representations of the images. The data representations have respective sub-arrays of data features that are based on respective features of the microarray. Each of the data features has a corresponding location relative to other data features and a signal value that is based on one or more of the light intensities. The method also includes combining the data representations of adjacent images based on a comparison of the signal values of the data features of the data representations of the adjacent images, thereby generating a data representation of the microarray. The method also includes analyzing the data representation of the microarray to determine properties or characteristics of a sample.

DETAILED DESCRIPTION OF THE INVENTION

Figure 1:
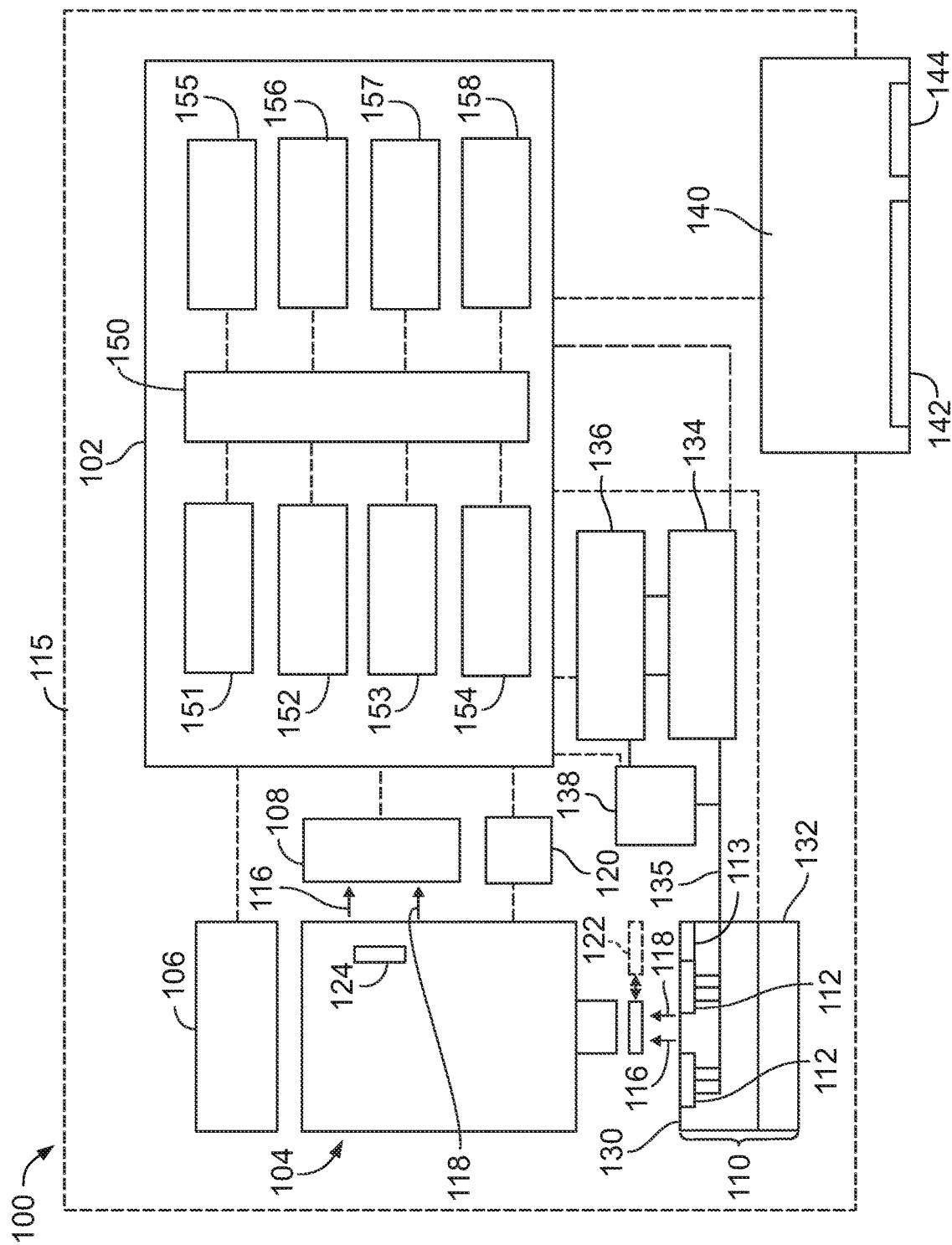
FIG. 1 is a block diagram of an assay system for performing biological or chemical assays formed in accordance with one embodiment.

Embodiments described herein include various methods and systems used to detect optical signals that are provided by samples. The optical signals may be light emissions that are generated in response to excitation light or light emissions that are generated by the label without excitation (e.g., a radioactive or chemiluminescent component in the sample). Particular embodiments include systems or components of systems that may be used in performing more than one type of assay protocol. For example, embodiments may be used to perform or facilitate performing a sequencing protocol in which sstDNA is sequenced in a flow cell and imaged and a microarray protocol in which microarrays are imaged to for various applications.

Components of the system may include carrier assemblies that are positioned on a system stage. The carrier assembly may be capable of holding different substrates having samples thereon. In particular embodiments, the carrier assembly is re-configurable such that one or more components may be added or removed. In a first configuration, the carrier assembly may be configured to hold a first substrate, such as a flow cell, during a sequencing protocol in which fluids are directed through the flow cell. The fluids flow across an interior surface of a flow channel while the flow cell is positioned on the system stage. The fluids deliver reagents to the sample on the interior surface. An optical system may then detect optical signals from the interior surface. In a second configuration, the carrier assembly may be configured to hold a second substrate, such as an open-face substrate, having a sample located on an exterior surface of the second substrate. The second substrate may include, for example, probes arranged in an array on an exterior surface of the second substrate. Unlike the flow cell, the second substrate may not have fluid flow across the exterior surface while the second substrate is positioned on the system stage. Accordingly, the carrier assembly may be configured to hold different substrates on the same system stage for different assay protocols. Although two particular configurations are described above, the carrier assembly may be capable of having different configurations than those described above and/or more than two configurations.

One or more aspects of the subject matter described herein may be similar to the subject matter described in U.S. Pat. Nos. 8,951,781; 8,748,789; 7,769,548; and 8,481,903 and in U.S. Patent Publ. No. 2013/0260372, each of which is incorporated herein by reference in its entirety.

As used herein, the term "optical signals" includes electromagnetic energy capable of being detected. The term includes light emissions from labeled biological or chemical substances and also includes transmitted light that is refracted or reflected by optical substrates. For example, samples may include encoded microparticles that transform the incident light into optical signals that identify the microparticle (or substances immobilized on the microparticles). The transformed optical signals may form a detectable pattern that represents a code of the illuminated microparticle. Optical signals may also include incident light that is directed onto the sample to excite labels or to be reflected/refracted by the sample.

Optical signals, including excitation radiation that is incident upon the sample and light emissions that are provided by the sample, may have one or more spectral patterns. For example, more than one type of label may be excited in an imaging session. In such cases, the different types of labels may be excited by a common excitation light source or may be excited by different excitation light sources that simultaneously provide incident light. Each type of label may emit optical signals having a spectral pattern that is different from the spectral pattern of other labels. For example, the spectral patterns may have different emission spectra. The light emissions may be filtered to separately detect the optical signals from other emission spectra. As used herein, when the term "different" is used with respect to emission spectra, the emission spectra may have wavelength ranges that at least partially overlap so long as at least a portion of one emission spectrum does not completely overlap the other emission spectrum. Different emission spectra may have other characteristics that do not overlap, such as emission anisotropy or fluorescence lifetime. When the light emissions are filtered, the wavelength ranges of the emission spectra may be narrowed.

In some embodiments, the optical signals are directed through an optical train having a plurality of optical components. The optical signals are directed to a detector (e.g., image sensor). In particular embodiments, the optical components of the optical train may be selectively moveable. As used herein, when the term "selectively" is used in conjunction with "moving" and similar terms, the phrase means that the position of the optical component may be changed in a desired manner. For example, at least one of the location and the orientation of the optical component may be changed. The phrase "selectively moving" includes removing the optical component from the optical path, adjusting an orientation of the optical component in the optical path (e.g., rotating the optical component), or moving the optical component such that the orientation does not change, but the location of the optical component does change. In particular embodiments, the optical components are selectively moved between imaging sessions. However, in other embodiments, the optical components may be selectively moved during an imaging session.

Different elements and components may be removably coupled. As used herein, when two or more elements or components are "removably coupled" (or "removably engaged") the elements are readily separable without destroying the coupled components. Elements are readily separable when the elements may be separated from each other without undue effort or a significant amount of time spent in separating the components. For example, in some embodiments, an adapter plate of a carrier assembly may be removably coupled to a support frame numerous times during the lifetime of the carrier assembly. When removably coupled, the adapter plate and the support frame may operate together in a suitable manner for holding a substrate. In particular embodiments, the elements are automatically removably coupled by a machine or system. Furthermore, in some embodiments, the removably coupled elements are directly attached to one another such that some contact is made between the coupled elements. In other embodiments, the removably coupled elements have intervening elements that facilitate removably coupling. For example, the adapter plate may be directly attached to a gasket or intervening layer that is directly attached to the support frame. Accordingly, the adapter plate and the support frame do not necessarily contact each other. Exemplary modes for removably coupling components include, but are not limited to, interactions mediated by frictional engagement (e.g., interference fit, snap-fit), magnetism, vacuum, charge, mild adhesives, mechanical clamping or the like.

In other embodiments, different elements and components may not be readily separable. For example, the support frame and adapter plate may be different portions of the same unitary body. The support frame and adapter plate may be injection-molded and shaped by a common mold. In some embodiments, the support frame and the adapter plate may be discrete components that are secured to each other in a manner such that the components are not readily separable. For example, one or more portions of the support frame and the adapter plate may be fused together. As used herein, the phrase "[Element A] coupled to [Element B]" may include Elements A and B being discrete components that are removably coupled to each other, secure to each other, or portions of the same unitary structure.

Imaging sessions include a time period in which at least a portion of the sample is imaged. One sample may undergo or be subject to multiple imaging sessions. For example, one sample may be subject to two different imaging sessions in which each imaging session attempts to detect optical signals from one or more different labels. As a specific example, a first scan along at least a portion of a nucleic acid sample may detect labels associated with nucleotides A and C and a second scan along at least a portion of the sample may detect labels associated with nucleotides G and T.

During an imaging session, optical signals provided by the sample are observed through an optical system. Various types of imaging may be used with embodiments described herein. For example, embodiments may be configured to perform at least one of epi-fluorescent imaging and total-internal-reflectance-fluorescence (TIRF) imaging. In particular embodiments, the sample imager is a scanning time-delay integration (TDI) system. Furthermore, the imaging sessions may include "line scanning" one or more samples such that a linear focal region of light is scanned across the sample(s). Some methods of line scanning are described, for example, in U.S. Pat. No. 7,329,860 and International Publication No. WO 2009/137435, of which the complete subject matter is incorporated herein by reference in their entirety. Imaging sessions may also include moving a point focal region of light in a raster pattern across the sample(s). Alternatively, one or more regions of the sample(s) may be illuminated at one time in a "step and shoot" manner. In other embodiments, imaging sessions may include detecting light emissions that are generated, without illumination, and based entirely on emission properties of a label within the sample (e.g., a radioactive or chemiluminescent component in the sample).

Systems that may be capable of carrying out one or more assay protocols described herein include systems developed by Illumina, Inc., such as the MiSeq, HiSeq 2500, HiSeq X Ten, NeoPrep, HiScan, NextSeq, and iScan systems. Systems capable of carrying out one or more of the assay protocols described herein are described in U.S. Pat. Nos. 8,951,781; 8,748,789; 7,769,548; and 8,481,903 and in U.S. Patent Publ. No. 2013/0260372, each of which is incorporated herein by reference in its entirety.

As used herein, the term "sample" includes various matters of interest that undergo an imaging session where optical signals from the sample are observed. In particular embodiments, a sample may include biological or chemical substances of interests. As used herein, the term "biological or chemical substances" may include a variety of biological or chemical substances that are suitable for being imaged or examined with the optical systems described herein. For example, biological or chemical substances include biomolecules, such as nucleosides, nucleic acids, polynucleotides, oligonucleotides, proteins, enzymes, polypeptides, antibodies, antigens, ligands, receptors, polysaccharides, carbohydrates, polyphosphates, nanopores, organelles, lipid layers, cells, tissues, organisms, and biologically active chemical compound(s) such as analogs or mimetics of the aforementioned species. Other chemical substances include labels that can be used for identification, examples of which include fluorescent labels and others set forth in further detail below.

Different types of samples may be coupled to different types of optical substrates or support structures that affect incident light in different manners. In particular embodiments, samples to be detected can be attached to one or more surfaces of a substrate or support structure. For example, open-face substrates (such as some microarrays and chips) have biological or chemical substances immobilized to an exterior surface of the open-face substrate. As such, optical signals to be detected are projected from an exterior surface through air and perhaps through liquid having different indices of refraction when the optical signals are collected from above. However, flow cells or capillary flow optical substrates may include one or more flow channels. In flow cells, the flow channels may be separated from the surrounding environment by top and bottom layers of the flow cell. Thus, optical signals to be detected are projected from within the support structure and may transmit through multiple layers of material having different refractive indices. For example, when detecting optical signals from an inner bottom surface of a flow channel and when detecting optical signals from above the flow channel, the optical signals that are desired to be detected may propagate through a fluid having an index of refraction, through one or more layers of the flow cells having different indices of refraction, and through the ambient environment having a different index of refraction. In some embodiments, the optical signals propagating from the open-face substrate may be affected differently than the optical signals propagating from a surface of the flow channel. In such cases, embodiments described herein may facilitate adjusting or modifying the optical train that directs the optical signals from the sample to the detector assembly. However, in other embodiments, the optical train is not adjusted for different samples. For example, the same optical train may detect optical signals from a flow cell and optical signals from an open-face substrate. Embodiments may adjust or modify the optical train as described in U.S. Pat. No. 8,481,903, which is incorporated herein by reference in its entirety.

Optical substrates or support structures include flow cells having flow channels where, for example, nucleic acids are sequenced. In other embodiments, optical substrates may include one or more slides, open-face substrates, planar chips (such as those used in microarrays), or microparticles. In such cases where the optical substrate includes a plurality of microparticles that support the biological or chemical substances, the microparticles may be held by another optical substrate, such as a slide, array of pits, or grooved plate. In particular embodiments, the optical substrate includes diffraction grating based encoded optical identification elements similar to or the same as those described in pending U.S. patent application Ser. No. 10/661,234, entitled Diffraction Grating Based Optical Identification Element, filed Sep. 12, 2003, which is incorporated herein by reference in its entirety, discussed more hereinafter. A bead cell or plate for holding the optical identification elements may be similar to or the same as that described in pending U.S. patent application Ser. No. 10/661,836, entitled "Method and Apparatus for Aligning Microbeads in Order to Interrogate the Same", filed Sep. 12, 2003, and U.S. Pat. No. 7,164,533, entitled "Hybrid Random Bead/Chip Based Microarray", issued Jan. 16, 2007, as well as U.S. patent application Ser. No. 60/609,583, entitled "Improved Method and Apparatus for Aligning Microbeads in Order to Interrogate the Same", filed Sep. 13, 2004, Ser. No. 60/610, 910, entitled "Method and Apparatus for Aligning Microbeads in Order to Interrogate the Same", filed Sep. 17, 2004, each of which is incorporated herein by reference in its entirety.

Optical systems described herein may also be used to scan samples that include microarrays. A microarray may include a population of different probe molecules that are attached to one or more substrates such that the different probe molecules can be differentiated from each other according to relative location. An array can include different probe molecules, or populations of the probe molecules, that are each located at a different addressable location on a substrate. Alternatively, a microarray can include separate optical substrates, such as beads, each bearing a different probe molecule, or population of the probe molecules, that can be identified according to the locations of the optical substrates on a surface to which the substrates are attached or according to the locations of the substrates in a liquid. Exemplary arrays in which separate substrates are located on a surface include, without limitation, a BeadChip Array available from Inc. (San Diego, Calif.) or others including beads in wells such as those described in U.S. Pat. Nos. 6,266,459, 6,355,431, 6,770,441, 6,859,570, and 7,622,294; and PCT Publication No. WO 00/63437, each of which is hereby incorporated by reference. Other arrays having particles on a surface include those set forth in US 2005/0227252; WO 05/033681; and WO 04/024328, each of which is hereby incorporated by reference.

Any of a variety of microarrays known in the art, including, for example, those set forth herein, can be used. A typical microarray contains reaction sites, sometimes referred to as features, each having a population of probes. The population of probes at each reaction site is typically homogenous having a single species of probe, but in some embodiments the populations can each be heterogeneous. Reaction sites or features of an array are typically discrete, being separated with spaces between each other. The size of the probe sites and/or spacing between the reaction sites can vary such that arrays can be high density, medium density or lower density. High density arrays are characterized as having reaction sites separated by less than about 15 µm. Medium density arrays have reaction sites separated by about 15 to 30 µm, while low density arrays have reaction sites separated by greater than 30 µm. An array useful in the invention can have reaction sites that are separated by less than 100 µm, 50 µm, 10 µm, 5 µm, 1 µm, or 0.5 µm. An apparatus or method of an embodiment of the invention can be used to image an array at a resolution sufficient to distinguish sites at the above densities or density ranges.

Further examples of commercially available microarrays that can be used include, for example, an Affymetrix® GeneChip® microarray or other microarray synthesized in accordance with techniques sometimes referred to as VLSIPS. (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752 and 6,482,591, each of which is hereby incorporated by reference. A spotted microarray can also be used in a method according to an embodiment of the invention. An exemplary spotted microarray is a CodeLink™ Array available from Amersham Biosciences. Another microarray that is useful is one that is manufactured using inkjet printing methods such as SurePrint™ Technology available from Agilent Technologies.

The systems and methods set forth herein can be used to detect the presence of a particular target molecule in a sample contacted with the microarray. This can be determined, for example, based on binding of a labeled target analyte to a particular probe of the microarray or due to a target-dependent modification of a particular probe to incorporate, remove, or alter a label at the probe location. Any one of several assays can be used to identify or characterize targets using a microarray as described, for example, in U.S. Patent Application Publication Nos. 2003/0108867; 2003/0108900; 2003/0170684; 2003/0207295; or 2005/0181394, each of which is hereby incorporated by reference.

Furthermore, optical systems described herein may be constructed to include various components and assemblies as described in PCT application PCT/US07/07991, entitled "System and Devices for Sequence by Synthesis Analysis", filed Mar. 30, 2007 and/or to include various components and assemblies as described in International Publication No. WO 2009/042862, entitled "Fluorescence Excitation and Detection System and Method", filed Sep. 26, 2008, both of which the complete subject matter are incorporated herein by reference in their entirety. In particular embodiments, optical systems can include various components and assemblies as described in U.S. Pat. No. 7,329,860 and WO 2009/137435, of which the complete subject matter is incorporated herein by reference in their entirety. Optical systems can also include various components and assemblies as described in U.S. patent application Ser. No. 12/638,770, filed on Dec. 15, 2009, of which the complete subject matter is incorporated herein by reference in its entirety.

In particular embodiments, methods, and optical systems described herein may be used for sequencing nucleic acids. For example, sequencing-by-synthesis (SBS) protocols are particularly applicable. In SBS, a plurality of fluorescently labeled modified nucleotides are used to sequence dense clusters of amplified DNA (possibly millions of clusters) present on the surface of an optical substrate (e.g., a surface that at least partially defines a channel in a flow cell). The flow cells may contain nucleic acid samples for sequencing where the flow cells are placed within the appropriate flow cell holders. The samples for sequencing can take the form of single nucleic acid molecules that are separated from each other so as to be individually resolvable, amplified populations of nucleic acid molecules in the form of clusters or other features, or beads that are attached to one or more molecules of nucleic acid. The nucleic acids can be prepared such that they comprise an oligonucleotide primer adjacent to an unknown target sequence. To initiate the first SBS sequencing cycle, one or more differently labeled nucleotides, and DNA polymerase, etc., can be flowed into/through the flow cell by a fluid flow subsystem (not shown). Either a single type of nucleotide can be added at a time, or the nucleotides used in the sequencing procedure can be specially designed to possess a reversible termination property, thus allowing each cycle of the sequencing reaction to occur simultaneously in the presence of several types of labeled nucleotides (e.g. A, C, T, G). The nucleotides can include detectable label moieties such as fluorophores. Where the four nucleotides are mixed together, the polymerase is able to select the correct base to incorporate and each sequence is extended by a single base. Nonincorporated nucleotides can be washed away by flowing a wash solution through the flow cell. One or more lasers may excite the nucleic acids and induce fluorescence. The fluorescence emitted from the nucleic acids is based upon the fluorophores of the incorporated base, and different fluorophores may emit different wavelengths of emission light. A deblocking reagent can be added to the flow cell to remove reversible terminator groups from the DNA strands that were extended and detected. The deblocking reagent can then be washed away by flowing a wash solution through the flow cell. The flow cell is then ready for a further cycle of sequencing starting with introduction of a labeled nucleotide as set forth above. The fluidic and detection steps can be repeated several times to complete a sequencing run. Exemplary sequencing methods are described, for example, in Bentley et al., Nature 456:53-59 (2008), WO 04/018497; U.S. Pat. No. 7,057,026; WO 91/06678; WO 07/123,744; U.S. Pat. Nos. 7,329,492; 7,211,414; 7,315,019; 7,405,281, and US 2008/0108082, each of which is incorporated herein by reference.

In some embodiments, nucleic acids can be attached to a surface and amplified prior to or during sequencing. For example, amplification can be carried out using bridge amplification. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420. Another useful method for amplifying nucleic acids on a surface is rolling circle amplification (RCA), for example, as described in Lizardi et al., Nat. Genet. 19:225-232 (1998) and US 2007/0099208 A1, each of which is incorporated herein by reference. Emulsion PCR on beads can also be used, for example as described in Dressman et al., Proc. Natl. Acad. Sci. USA 100:8817-8822 (2003), which is incorporated herein by reference.

Other sequencing techniques that are applicable for use of the methods and systems set forth herein are pyrosequencing, nanopore sequencing, and sequencing by ligation. Exemplary pyrosequencing techniques and samples that are particularly useful are described in U.S. Pat. Nos. 6,210,891; 6,258,568; 6,274,320 and Ronaghi, Genome Research 11:3-11 (2001), each of which is incorporated herein by reference. Exemplary nanopore techniques and samples that are also useful are described in Deamer et al., Acc. Chem. Res. 35:817-825 (2002); Li et al., Nat. Mater. 2:611-615 (2003); Soni et al., Clin Chem. 53:1996-2001 (2007) Healy et al., Nanomed. 2:459-481 (2007) and Cockroft et al., J. am. Chem. Soc. 130:818-820; and U.S. Pat. No. 7,001,792, each of which is incorporated herein by reference. In particular, these methods utilize repeated steps of reagent delivery. An instrument or method set forth herein can be configured with reservoirs, valves, fluidic lines and other fluidic components along with control systems for those components in order to introduce reagents and detect signals according to a desired protocol such as those set forth in the references cited above. Any of a variety of samples can be used in these systems such as substrates having beads generated by emulsion PCR, substrates having zero-mode waveguides, substrates having integrated CMOS detectors, substrates having biological nanopores in lipid bilayers, solid-state substrates having synthetic nanopores, and others known in the art. Such samples are described in the context of various sequencing techniques in the references cited above and further in US 2005/0042648; US 2005/0079510; US 2005/0130173; and WO 05/010145, each of which is incorporated herein by reference.

Exemplary labels that can be detected in accordance with various embodiments, for example, when present on or within a support structure include, but are not limited to, a chromophore; luminophore; fluorophore; optically encoded nanoparticles; particles encoded with a diffraction-grating; electrochemiluminescent label such as Ru(bpy).sup.32+; or moiety that can be detected based on an optical characteristic. Fluorophores that may be useful include, for example, fluorescent lanthanide complexes, including those of Europium and Terbium, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue™, Texas Red, alexa dyes, phycoerythin, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066, each of which is hereby incorporated by reference. In some embodiments, the one pair of labels may be excitable by a first excitation wavelength and another pair of labels may be excitable by a second excitation wavelength.

Although embodiments are exemplified with regard to detection of samples that include biological or chemical substances supported by an optical substrate, it will be understood that other samples can be imaged by the embodiments described herein. Other exemplary samples include, but are not limited to, biological specimens such as cells or tissues, electronic chips such as those used in computer processors, and the like. Examples of some of the applications include microscopy, satellite scanners, high-resolution reprographics, fluorescent image acquisition, analyzing and sequencing of nucleic acids, DNA sequencing, sequencing-by-synthesis, imaging of microarrays, imaging of holographically encoded microparticles and the like.

FIG. 1 is a block diagram of an assay system 100 for biological or chemical analysis formed in accordance with one embodiment. The assay system 100 may be a workstation that may be similar to a bench-top device or desktop computer. For example, a majority of the systems and components for conducting the desired reactions can be within a common housing 115 of the assay system 100. In some embodiments, the assay system 100 includes one or more components, assemblies, or systems that are remotely located from the assay system 100. Furthermore, the assay system 100 may include various components, assemblies, and systems (or sub-systems) that interact with each other to perform one or more predetermined methods or assay protocols for biological or chemical analysis. In some embodiments, the protocols may be performed in an automated manner without user interaction after the protocol has begun.

For example, the assay system 100 includes a system controller 102 that may communicate with the various components, assemblies, and sub-systems of the assay system 100. As shown, the assay system 100 has an optical system 104, an excitation source assembly 106, a detector assembly 108, and a docking station or system 110 that supports one or more carrier assemblies 112 having substrates with samples thereon. In some embodiments, the optical system 104 includes the excitation source assembly 106 and/or the detector assembly 108. In some embodiments, the optical system 104 is configured to direct incident light from the excitation source assembly 106 onto the sample(s). The excitation source assembly 106 may include one or more excitation light sources that are configured to excite labels associated with the samples. The excitation source assembly 106 may also be configured to provide incident light that is reflected and/or refracted by the samples. As shown, the samples may provide optical signals that include light emissions 116 and/or transmission light 118. The docking system 110 and the optical system 104 may be moved relative to each other. In particular embodiments, the docking system 110 includes a system stage 130 and a motor assembly 132 that moves the system stage 130 with respect to the optical system 104. In other embodiments, the motor assembly 132 may be operably coupled to the optical system 104 and may move the optical system 104 in addition to or alternatively to the docking system 110. The optical system 104 may be or include an optical train having a plurality of optical components.

The optical system 104 may also be configured to direct the light emissions 116 and/or transmission light 118 to the detector assembly 108. The detector assembly 108 may include one or more image sensors. The image sensors may be, by way of example only, CMOS imagers, CCD cameras, or photodiodes. The optical system 104 may include an optics adjustment system (or sub-system) 120. The optics adjustment system 120 is configured to selectively move one or more optical components of the optical system 104. For example, the optics adjustment system 120 may selectively move a path compensator 122 and/or an optical device 124 that is located upstream or downstream from the sample. Components can also be shared among two or more optical trains. For example, one or more components can be alternatively placed into contact with different optical paths (e.g. emissions from different samples).

Also shown, the assay system 100 may include a fluidic control system 134 to control the flow of fluid throughout a fluidic network 135 (indicated by the solid lines) of the assay system 100. The fluidic control system 134 may deliver reagents to the sample during, for example, a sequencing protocol. The assay system 100 may also include a fluid storage system 136 that is configured to hold fluids that may be used by the assay system 100 and a temperature control system 138 that regulates the temperature of the fluid. The temperature control system 138 may also generally regulate a temperature of the assay system 100 using, for example, heat sinks, and blowers. Exemplary temperature control systems are described in U.S. Ser. No. 12/565,606, which is incorporated herein by reference.

In some embodiments, the fluidic network 135 includes one or more umbilical cables (not shown) that operatively couples the fluidic control system 134 and the fluidic storage system 136 to the system stage 130 and other components of the assay system 100. The carrier assembly 112 may comprise a flow cell that is configured to have solutions flow therethrough during an assay protocol. The solutions may be delivered through the umbilical cable. For example, the umbilical cable may be fluidicly coupled to the flow cell and a multi-port pump, which is, in turn, fluidically coupled to various fluids (e.g., reagents, buffers, and others) in the fluid storage system 136. The pump may receive instructions for delivering different solutions to the flow cell. The umbilical cable may include one or more fluidic lines and also one or more communication lines (e.g., electrical or optical) that deliver instructions.

Also shown, the assay system 100 may include a user interface 140 that interacts with the user. For example, the user interface 140 may include a display 142 to display or request information from a user and a user input device 144 to receive user inputs. In some embodiments, the display 142 and the user input device 144 are the same device (e.g., touchscreen). As will be discussed in greater detail below, the assay system 100 may communicate with various components to perform the desired reactions. The assay system 100 may also be configured to analyze the detection data to provide a user with desired information.

The fluidic control system 134 is configured to direct and regulate the flow of one or more fluids through the fluidic network 135. The fluidic network 135 may be in fluid communication with at least one of the substrates and the fluid storage system 136. For example, select fluids may be drawn from the fluid storage system 136 and directed to the carrier assembly 112 having the substrate in a controlled manner, or the fluids may be drawn from the substrate and directed toward, for example, a waste reservoir in the fluid storage system 136. Although not shown, the fluidic control system 134 may include flow sensors that detect a flow rate or pressure of the fluids within the fluid network. The sensors may communicate with the system controller 102.

The temperature control system 138 is configured to regulate the temperature of fluids at different regions of the fluidic network 135, the fluid storage system 136, and/or the substrate. For example, the temperature control system 138 may include a thermocycler (not shown) that interfaces with the substrate (or carrier assembly 112) and controls the temperature of the fluid that flows along the sample. The temperature control system 138 may also regulate the temperature of solid elements or components of the assay system 100 or sample. Although not shown, the temperature control system 138 may include sensors to detect the temperature of the fluid or other components. The sensors may communicate with the system controller 102.

The fluid storage system 136 is in fluid communication with the sample and may store various reaction components or reactants that are used to conduct the desired reactions therein. The fluid storage system 136 may store fluids for washing or cleaning the fluidic network 135 or the sample and also for diluting the reactants. For example, the fluid storage system 136 may include various reservoirs to store reagents, enzymes, other biomolecules, buffer solutions, aqueous, and non-polar solutions, and the like. Furthermore, the fluid storage system 136 may also include waste reservoirs for receiving waste products.

The docking system 110 is configured to engage one or more carrier assemblies 112, for example, in at least one of a mechanical, electrical, and fluidic manner. The docking system 110 may hold the carrier assemblies 112 in a desired orientation to facilitate the flow of fluid through the carrier assemblies 112 and/or imaging of the sample. Docking systems can be configured to deliver fluids to one sample, but not to another. The system can be configured to deliver different fluids to different samples. Alternatively or additionally, fluids can be delivered to different samples in a different temporal sequence, amount, flow rate, or duration. In some embodiments, the docketing system 110 includes a carrier sensor 113. The carrier sensor 113 may determine a type of sample by, for example, scanning a barcode on the substrate of the carrier assembly 112 or by detecting RF signals from an RFID tag that identifies the type of sample.

The system controller 102 may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. The functions may be executed within a commercially reasonable time period. The above examples are exemplary only, and are thus not necessarily intended to limit in any way the definition and/or meaning of the term system controller. In the exemplary embodiment, the system controller 102 executes a set of instructions that are stored in one or more storage elements, memories, or modules in order to at least one of obtain and analyze detection data. Storage elements may be in the form of information sources or physical memory elements within the assay system 100. Embodiments include non-transitory computer-readable media that include set of instructions for performing or executing one or more processes set forth herein. Non-transitory computer readable media may include all computer-readable media, except for transitory propagating signals per se. The non-transitory computer readable media may include generally any tangible computer-readable medium including, for example, persistent memory such as magnetic and/or optical disks, ROM, and PROM and volatile memory such as RAM. The computer-readable medium may store instructions for execution by one or more processors.

The set of instructions may include various commands that instruct the assay system 100 to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Components of the assay system may include or represent hardware circuits or circuitry that include and/or are connected with one or more processors, such as one or more computer microprocessors. The operations of the methods described herein and the assay system can be sufficiently complex such that the operations cannot be mentally performed by an average human being or a person of ordinary skill in the art within a commercially reasonable time period.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the assay system 100, processed in response to user inputs, or processed in response to a request made by another processing machine (e.g., a remote request through a communication link).

The system controller 102 may be connected to the other components or sub-systems of the assay system 100 via communication links (indicated by dashed lines). The system controller 102 may also be communicatively connected to off-site systems or servers. The communication links may be hardwired or wireless. The system controller 102 may receive user inputs or commands, from the user interface 140. The user input device 144 may include a keyboard, mouse, a touch-screen panel, and/or a voice recognition system, and the like. Alternatively or in addition, the user input device 144 may also be the display 142.

In some embodiments, the assay system 100 may have interchangeable or swappable devices (e.g., plug-and-play). For example, the docking system 110 or system stage 130 may be readily replaced or substituted with a different docking system 110 or system stage 130. This may occur when a different type of sample is desired to be used. In some embodiments, the sample is readily exchanged from the system stage 130. Furthermore, the fluid storage system 136 may be a container that is readily separated from the fluid network and replaced by another container. This may occur when the fluid in the container is depleted, has expired, or a different container is required because a user of the assay system 100 desires to run a different assay protocol. Furthermore, the system controller 102 may have swappable devices (e.g., if the user desires to use the assay system 100 to execute a different assay protocol).

FIG. 1 also illustrates a block diagram of the system controller 102. In one embodiment, the system controller 102 includes one or more processors or modules that can communicate with one another. The system controller 102 is illustrated conceptually as a collection of modules, but may be implemented utilizing any combination of dedicated hardware boards, DSPs, processors, etc. Alternatively, the system controller 102 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

The system controller 102 may include a plurality of modules 151-158 that communicate with a system control module 150. The system control module 150 may communicate with the user interface 140. Although the modules 151-158 are shown as communicating directly with the system control module 150, the modules 151-158 may also communicate directly with each other, the user interface 140, or the other systems. Also, the modules 151-158 may communicate with the system control module 150 through the other modules.

The plurality of modules 151-158 include system modules 151-153 that communicate with the sub-systems. The fluidic control module 151 may communicate with the fluidic control system 134 to control the valves and flow sensors of the fluidic network 135 for controlling the flow of one or more fluids through the fluidic network 135. The fluid storage module 152 may notify the user when fluids are low or when the waste reservoir must be replaced. The fluid storage module 152 may also communicate with the temperature control module 153 so that the fluids may be stored at a desired temperature.

The plurality of modules 151-158 may also include an optics adjustment (or correction) module 154 that communicates with the optics adjustment system 120 and an identification module 155 that determines identification information relating to the sample. For example, the carrier assembly 112 may be scanned before an imaging session or before being placed onto the system stage 130 to identify the type of sample. The optics adjustment module 154 may communicate with the various devices that are capable of selectively moving the optical components, such as a transfer device or a rotatable optical device. The plurality of modules 151-158 may also include a detection data analysis module 158 that receives and analyzes the detection data (e.g., image data) from the detector assembly 108. The processed detection data may be stored for subsequent analysis or may be transmitted to the user interface 140 to display desired information to the user. Furthermore, there may be a sample module that communicates with the sample (e.g., receives signals regarding temperature of the sample or flow rate of a fluid in the sample).

Protocol modules 156 and 157 communicate with the system control module 150 to control the operation of the sub-systems when conducting predetermined assay protocols. The protocol modules 156 and 157 may include sets of instructions for instructing the assay system 100 to perform specific operations pursuant to predetermined protocols. The protocol modules 156 and 157 include a sequencing-by-synthesis (SBS) module 156 that may be configured to issue various commands for performing sequencing-by-synthesis processes. In some embodiments, the SBS module 156 may also process detection data. The protocol module 157 may be configured to scan microarrays or perform other assay protocols.

By way of one example, the SBS module 156 may be configured to issue commands for sequencing-by-synthesis processes. For example, the SBS module 156 may issue commands to perform bridge PCR where clusters of clonal amplicons are formed on localized areas within a channel (or lane) of a flow cell. After generating the amplicons through bridge PCR, the SBS module 156 may provide instructions to linearize or denature the amplicons to make sstDNA and to add a sequencing primer such that the sequencing primer may be hybridized to a universal sequence that flanks a region of interest. Each sequencing cycle extends the sstDNA by a single base and is accomplished by modified DNA polymerase and a mixture of four types of nucleotides delivery of which can be instructed by the SBS module 156. The different types of nucleotides have unique fluorescent labels, and each nucleotide has a reversible terminator that allows only a single-base incorporation to occur in each cycle. After a single base is added to the sstDNA, the SBS module 156 may instruct a wash step to remove nonincorporated nucleotides by flowing a wash solution through the flow cell. The SBS module 156 may further instruct the excitation source assembly and detector assembly to perform an image session(s) to detect the fluorescence in each of the four channels (i.e., one for each fluorescent label). After imaging, the SBS module 156 may instruct delivery of a deblocking reagent to chemically cleave the fluorescent label and the terminator from the sstDNA. The SBS module 156 may instruct a wash step to remove the deblocking reagent and products of the deblocking reaction. Another similar sequencing cycle may follow. In such a sequencing protocol, the SBS module 156 may instruct the fluidic control system 134 to direct a flow of reagent and enzyme solutions through the sample.

In some embodiments, the SBS module 156 may also be configured to issue various commands for performing the steps of a pyrosequencing protocol. In this case, the sample may include millions of wells where each well has a single capture bead having clonally amplified sstDNA thereon. Each well may also include other smaller beads that, for example, may carry immobilized enzymes (e.g., ATP sulfurylase and luciferase) or facilitate holding the capture bead in the well. The SBS module 156 may be configured to issue commands to the fluidic control module 151 to run consecutive cycles of fluids that carry a single type of nucleotide (e.g., 1st cycle: A; 2nd cycle: G; 3rd cycle: C; 4th cycle: T; 5th cycle: A; 6th cycle: G; 7th cycle: C; 8th cycle: T; and on). When a nucleotide is incorporated into the DNA, pyrophosphate is released thereby instigating a chain reaction where a burst of light is generated. The burst of light may be detected by a sample detector of the detector assembly. Detection data may be communicated to the system control module 150, the detection data analysis module 158, and/or the SBS module 156 for processing. The detection data may be stored for later analysis or may be analyzed by the system controller 102 and an image may be sent to the user interface 140.

The protocol module 157 may be configured to send instructions for scanning a microarray for an unknown analyte. Before or after performing an imaging session, the protocol module 157 may instruct the optics adjustment system 120 to move an optical component within, into, or out of the optical path. For example, the protocol module 157 may request that the path compensator 122 be inserted into or removed from the optical path. The protocol module 157 may also request that another optical component be repositioned. Any of a variety of movable or adjustable optical components set forth herein can be moved, adjusted or otherwise manipulated in response to instructions sent from protocol module 157 or any other appropriate module of a system controller. Once the collective arrangement of the optical components is established as desired, the protocol module 157 may instruct the excitation source assembly to provide incident light onto the samples and the detector assembly to detect the optical signals provided by the sample.

In some embodiments, the user may provide user inputs through the user interface 140 to select an assay protocol to be run by the assay system 100. In other embodiments, the assay system 100 may automatically detect the type of sample that has been inserted into the docking system 110 and confirm with the user the assay protocol to be run. For example, the carrier sensor 113 may identify the type of sample in the carrier assembly by scanning or detecting signals from the substrate or the carrier assembly. Alternatively, the assay system 100 may offer a limited number of assay protocols that could be run with the determined type of sample. The user may select the desired assay protocol, and the assay system 100 may then perform the selected assay protocol based on preprogrammed instructions.

Figure 2:
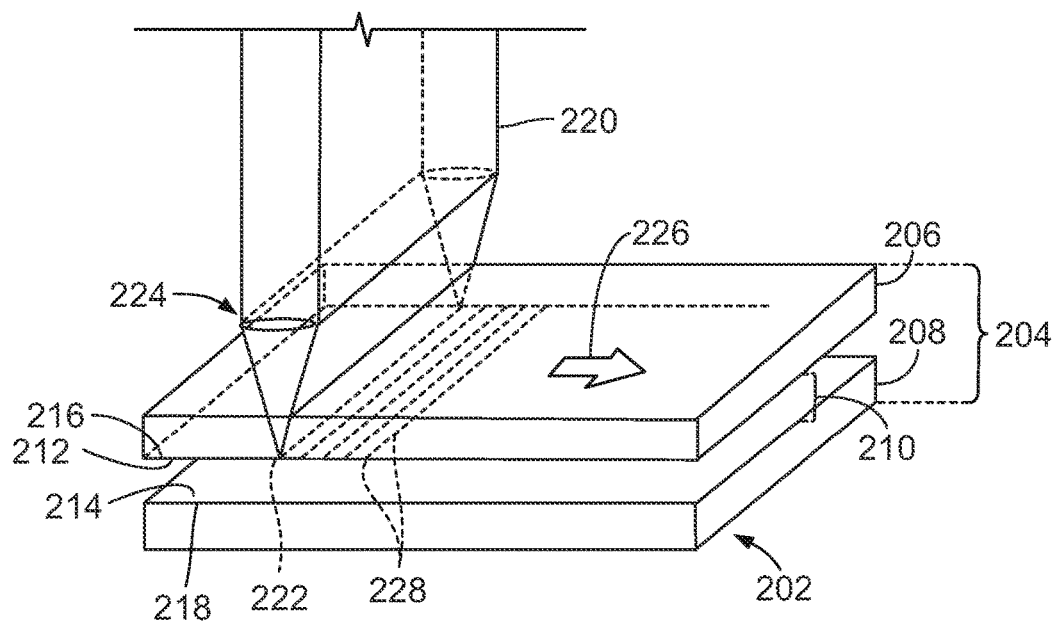
FIG. 2 is a diagram showing a perspective view of imaging a sample in accordance with one embodiment.
Figure 3:
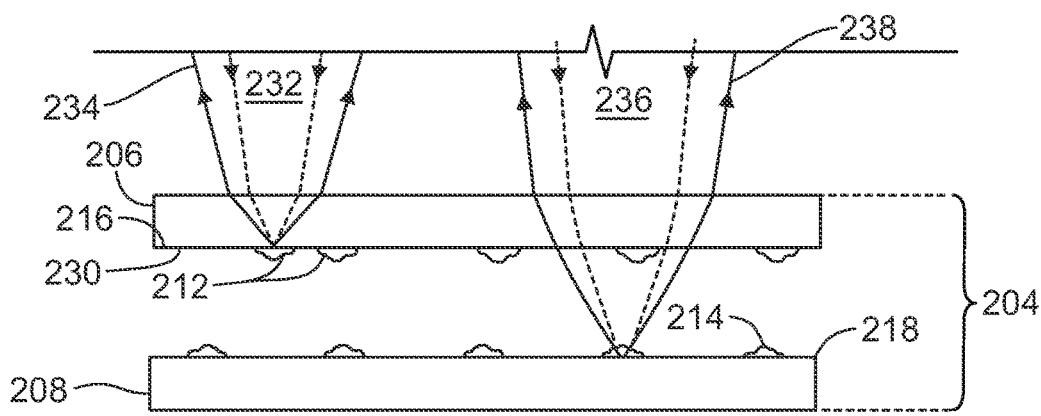
FIG. 3 is a side cross-sectional view of the diagram in FIG. 2.

FIGS. 2 and 3 are diagrams showing a perspective view and a side cross-sectional view, respectively, of imaging a sample 202 in accordance with one embodiment. In the illustrated embodiment, the sample 202 includes an optical substrate 204 that is represented as a flow cell. However, in alternative embodiments, the sample 202 may include a microarray as described above. As shown, the optical substrate 204 may include a first plate or layer 206 and a second plate or layer 208 with an interior volume or channel 210 extending between the first and second layers 206 and 208. The interior channel 210 may be configured to permit a flow of reagents therethrough. The first and second layers 206 and 208 may be formed from a variety of substrate materials. The substrate materials may be substantially transparent to wavelengths of the incident light and the optical signals that are provided from the sample. For example, the substrate materials may be substantially transparent to the optical signals emitted by one or more labels in the sample or may be substantially transparent to the optical signals that are reflected and or refracted by the sample. The first and second layers 206 and 208 may have biological components 212 and 214, respectively, on their corresponding interior surfaces 216 and 218.

In various embodiments, the sample 202 may be irradiated by excitation light or radiation 220 along a linear focal region 222 (also called a radiation line). However, in other embodiments, the focal region may have other configurations (e.g., point, oval). The focal region 222 may be formed by the excitation radiation 220 from one or more excitation light sources through an objective lens 224. The excitation light sources may generate light beams that are processed and shaped to provide a focal region 222 on the sample 202. The focused light beams may include optical signals having different emission spectra that excite associated fluorophores of the biological components 212 and 214. When excited, the fluorophores emit optical signals that may have different emission spectra. In some embodiments, the optical system may first direct the excitation radiation 220 toward the interior surface 216 of the optical substrate 204 to irradiate the biological components 212. In addition, the optical substrate 204 and the objective lens 224 may be moved in a relative manner with respect to each other such that the sample 202 is translated in a direction as indicated by the arrow 226. As such, the focal region 222 may progressively irradiate the biological components along the interior surface 216. As the focal region 222 translates along the interior surface 216, the focused light beams may successively scan regions 228 thereby scanning the entire interior surface 216 of the optical substrate 204. After scanning the interior surface 216, the objective lens 224 and the sample 202 may be moved with respect to each other and the same process may be repeated to scan the interior surface 218 of the optical substrate 204.

In particular embodiments, an apparatus or method can detect features on a surface at a rate of at least about 0.01 mm/sec. Depending upon the particular application, faster rates can also be used including, for example, in terms of the area scanned or otherwise detected, a rate of at least about 0.02 mm2/sec, 0.05 mm2/sec, 0.1 mm2/sec, 1 mm2/sec, 1.5 mm2/sec, 5 mm2/sec, 10 mm2/sec, 50 mm2/sec, 100 mm2/sec, or faster. If desired, for example, to reduce noise, the detection rate can have an upper limit of about 0.05 mm2/sec, 0.1 mm2/sec, 1 mm2/sec, 1.5 mm2/sec, 5 mm2/sec, 10 mm2/sec, 50 mm2/sec, or 100 mm2/sec.

In some embodiments, biological material may be immobilized on the multiple surfaces of the optical substrate 204. For instance, FIG. 3 illustrates the optical substrate 204 having biological components 212 and 214 attached to the interior surfaces 216 and 218, respectively. In the illustrated embodiment, an attachment layer 230 may be formed on both interior surfaces 216 and 218. The attachment layer 230 may facilitate immobilizing the biological components 212 and 214 thereto. As shown, a first excitation radiation 232 may be used to irradiate biological components 212 on the interior surface 216 of the optical substrate 204. Light emissions 234 from the irradiated biological components 212 may return through layer 206. Simultaneously or sequentially, a second excitation radiation 236 may be used to irradiate the biological components 214 on the interior surface 218 of the optical substrate 204. Light emissions 238 may return from the irradiated biological components 214 through the channel 210 and the layer 206.

In particular embodiments, path compensators may be used when imaging samples through objective lenses having high numerical aperture (NA) values. Exemplary high NA ranges include NA values of at least about 0.6. For example, the NA value may be at least about 0.65, 0.7, 0.75, 0.8, 0.85, 0.9, 0.95, or higher. Those skilled in the art will appreciate that NA, being dependent upon the index of refraction of the medium in which the lens is working, may be higher including, for example, up to 1.0 for air, 1.33 for pure water, or higher for other media such as oils. The compensator may also find use in objectives having lower NA values than the examples listed above. In general, the NA value of an objective lens is a measure of the breadth of angles for which the objective lens may receive light. The higher the NA value, the more light that may be collected by the objective lens for a given fixed magnification. As a result, multiple objects may be distinguished more readily when using objective lens with higher NA values because a higher feature density may be possible.

Figure 4:
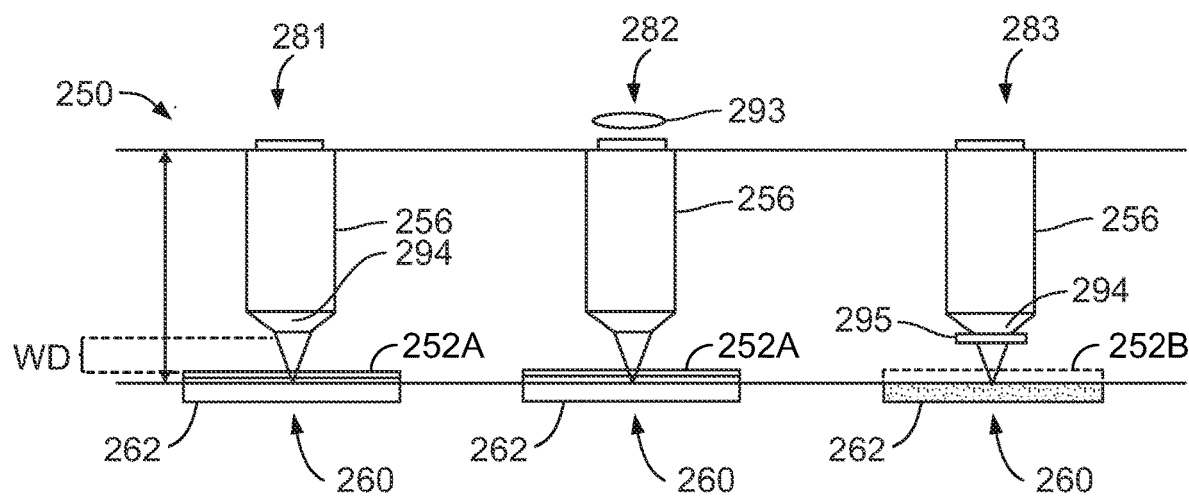
FIG. 4 illustrates various optical configurations that may be used for different imaging sessions.

FIG. 4 illustrates different optical configurations 281-283 of an optical system 250 that may be used during different imaging sessions. The optical system 250 includes an objective lens 256 having a collecting end 294. Also shown, a carrier assembly 260 is positioned proximate to the collecting end 294 of the objective lens 256. The carrier assembly 260 may include a first substrate 252A or a second substrate 252B. In an exemplary embodiment, the first substrate 252A is a flow cell, and the second substrate 252B is an open-face substrate. As will be described in greater detail below, embodiments described herein include adjustable or modifiable optical systems and assemblies. For example, a collective arrangement of the optical components that affect the optical signals provided by the sample may be changed for different imaging sessions. Changing a collective arrangement of the optical components causes a change in the propagation of the optical signals from the sample or a change in the spectrum of optical signals detected. The collective arrangements may be modified by removing or repositioning one or more of the optical components. Furthermore, the collective arrangements may be modified by exchanging filters along the optical path so that different optical signals are detected by a detector assembly.

As shown, a working distance WD may exist between a sample 252A and collecting end 294 of an objective lens 256. In some embodiments, the working distance WD is less than about 5000 microns. In particular embodiments, the working distance WD is less than about 2000 microns and, more particularly, less than about 1000 microns.

In FIG. 4, the carrier assembly 260 includes an identical support frame 262 for supporting the first and second substrates 252A and 252B. When supporting the second substrate 252B, the carrier assembly 260 may also include an adapter plate (not shown). In an exemplary embodiment, the first substrate 252A includes a flow cell having flow channels that are at least partially defined by first and second layers of material. The optical signals propagate from labels within the flow channels through one or more layers and possibly fluid to the exterior surface of the flow cell. The optical signals then propagate from the exterior surface to the objective lens. However, the second substrate 252B may be an open-face substrate such that the labels are located proximate to corresponding exterior surfaces of the open-face substrates and provide optical signals therefrom. In some cases, the optical signals that are emitted from the labels of the first and second substrates 252A, 252B will be affected differently before reaching the objective lens 256 due to the structures of the first and second substrates 252A, 252B. Accordingly, embodiments described herein may change the collective arrangement of the optical system so that the optical signals may be suitably detected.

The different optical configurations 281-283 shown in FIG. 4 represent specific examples of how path compensators 293 and 295 may be selectively moved to provide different collective arrangements. The path compensators 293 and 295 adjust the optical path of the optical signals that are provided by the samples. In various embodiments, optical components may be selectively moved so that a path compensator 295 may be located between the second substrate 252B and the objective lens 256 and/or a path compensator 293 may be located in an afocal position with respect to the objective lens 256.

As shown, the optical configuration 281 includes the objective lens 256 without any optical components (e.g., path compensators) located in the afocal position or between the objective lens 256 and the first substrate 252A. By way of example, the optical configuration 281 may be used during imaging sessions in which it is desired to image a bottom surface of a flow channel in the flow cell as shown in FIG. 4. When imaging a bottom surface of the flow channel, the input optical signals are transmitted through a top layer of the flow cell and then through the cavity defined between the top and bottom layers. After imaging the bottom surface of the flow channel, the assay system may move to image other surfaces of the sample (e.g., a top surface of the flow channel or an exterior surface of the flow cell or another sample). In such cases, the optical signals are no longer being transmitted through the top layer and the cavity. More specifically, if the assay system subsequently images a top surface of the flow channel or an exterior surface of a different sample, then it may be desirable to adjust the optical path or focal region to compensate for the reduced layers.

As such, the optical configuration 282 includes the path compensator 293 located at the afocal position with respect to the objective lens 256. The path compensator 293 may be selectively moved to the afocal position by a transfer device, such as transfer devices that are similar to the transfer devices described in US 2009/0272914 or U.S. Pat. No. 8,481,903, which are each incorporated herein by reference. The optical configuration 282 may be used during imaging sessions in which it is desired to image a top surface of a flow channel in the flow cell.

The optical configuration 283 includes the path compensator 295 being located between a collecting end 294 of the objective lens 256 and the second substrate 252B at an imaging position. In the imaging position, the path compensator 295 and the collecting end 294 may be spaced apart from each other by a fixed distance. However, the path compensator 295 and the second substrate 252B may be spaced apart by an adjustable distance. More specifically, the second substrate 252B and the objective lens 256 may be movable to and from each other during imaging sessions.

The path compensator 295 may be selectively moved to the imaging position by a transfer device. The path compensator 295 may have a fixed position with respect to the objective lens 256 during imaging sessions. In some embodiments, the path compensator 295 is operatively coupled to the objective lens 256 through one or more intervening components. In alternative embodiments, the path compensator 295 is directly attached to the collecting end 294 of the objective lens 256. The optical configuration 283 may be used to scan, for example, an exterior surface of a microarray.

Figure 5:
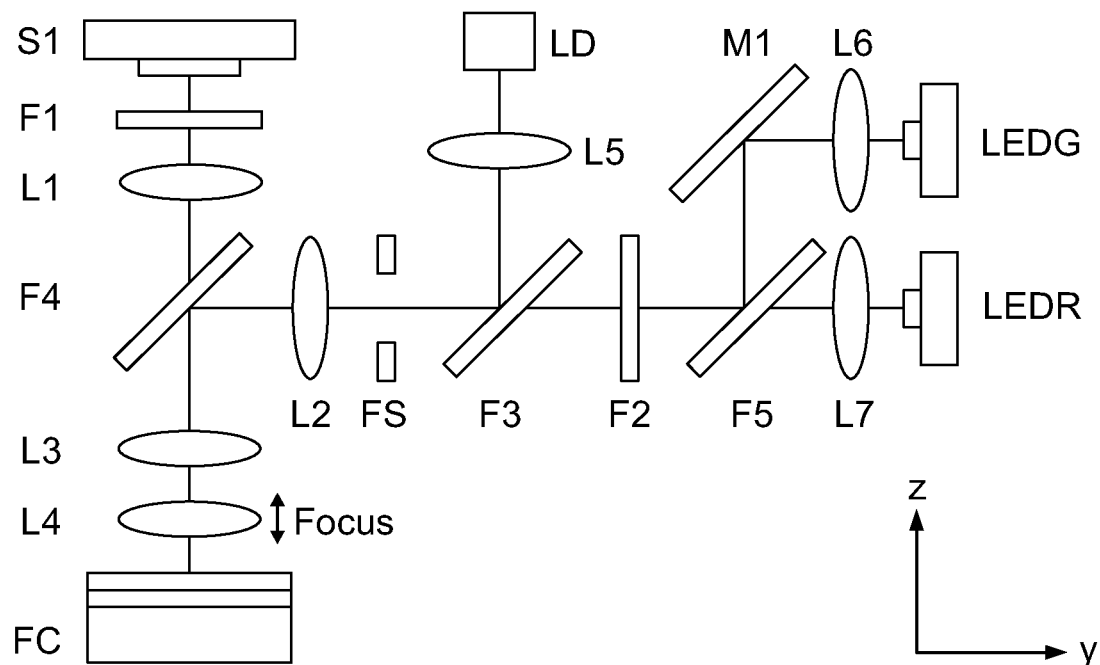
FIG. 5 shows an optical layout for a microfluorometer.

FIG. 5 shows an exploded view of an exemplary microfluorometer for purposes of demonstrating functional arrangement for at least some optical components. Two excitation sources are shown, including a green LED (LEDG) and a red LED (LEDR). Excitation light from each passes through a green LED collector lens (L6) and red LED collector lens (L7), respectively. An LED fold mirror (M1) reflects the green excitation radiation to a combiner dichroic (F5) which reflects the green excitation radiation through an excitation filter (F2), then through a laser diode beam splitter (F3), then through an excitation field stop (FS), then through an excitation projection lens group L2 to an excitation/emission dichroic (F4) which reflects the green excitation radiation through a stationary objective lens group (L3) and a translating objective lens group (L4) to the surface of a flow cell (FC). The red excitation radiation passes from the red LED collector lens (L7) to the combiner dichroic (F5) after which the red excitation radiation follows the same path as the green excitation radiation to the surface of the flow cell (FC). As shown in the figure, focusing is actuated by moving the translating objective lens group (L4) up and down (i.e. along the z dimension). Emission from the flow cell (FC) surface passes back through the translating objective lens group (L4), and then through the stationary objective lens group (L3) to the excitation/emission dichroic (F4) which passes the emission radiation to the emission projection les group (L1) through to the emission filter and then to the CMOS image sensor (S1). A laser diode (LD) is also directed via a laser diode coupling lens group (L5) to the laser diode beam splitter (F3) which reflects the laser diode radiation through the excitation field stop (FS), the excitation projection lens group (L2), the excitation/emission dichroic (F4), the stationary objective lens group (L3) and the translating objective lens group (L4) to the flow cell (FC).

As demonstrated by the exemplary embodiments of FIG. 5, each of the microfluorometers can include a beam splitter and a detector, wherein the beam splitter is positioned to direct excitation radiation from an excitation radiation source to the objective lens and to direct emission radiation from the objective to the detector. Each microfluorometer can optionally include an excitation radiation source such as an LED. In this case, each microfluorometer can include a dedicated radiation source, such that the read head includes several radiation sources each separated into individual microfluorometers. In some embodiments, two or more microfluorometers can receive excitation radiation from a common radiation source. As such the two or more microfluorometers can share a radiation source. In an exemplary configuration, a single radiation source can direct radiation to a beam splitter that is positioned to separate the excitation radiation into two or more beams and directs the beams to two or more respective microfluorometers. Additionally or alternatively, excitation radiation can be directed from a radiation source to one, two or more microfluorometers via one or more optical fibers.

It will be understood that the particular components shown in the figures are exemplary and can be replaced with components of similar function. For example, any of a variety of radiation sources can be used instead of an LED. Particularly useful radiation sources are arc lamps, lasers, semiconductor light sources (SLSs), or laser diodes. LEDs can be purchased, for example, from Luminus (Billerica, Mass.). Similarly, a variety of detectors are useful including, but not limited to a charge-coupled device (CCD) sensor; photomultiplier tubes (PMT's); or complementary metal-oxide-semiconductor (CMOS) sensor. A particularly useful detector is a 5-megapixel CMOS sensor (MT9P031) available from Aptina Imaging (San Jose, Calif.).

FIG. 5 provides exemplary embodiments of a microfluorometer that includes two excitation sources. This configuration is useful for detecting at least two fluorophores that are excited at different wavelengths, respectively. If desired, a microfluorometer can be configured to include more than two excitation sources. For example, a microfluorometer can include at least 2, 3, 4 or more different excitation sources (i.e. sources producing different wavelengths from each other). Alternatively or additionally, beam splitters and optical filters can be used to expand the range of excitation wavelengths available from an individual radiation source. Similar use of multiple radiation sources and/or optical filtering of split excitation beams can be used for embodiments where several microfluorometers share excitation from one or more radiation sources. As set forth in further detail elsewhere herein, the availability of multiple excitation wavelengths is particularly useful for sequencing applications that utilize several different fluorophore labels.

Figure 6:
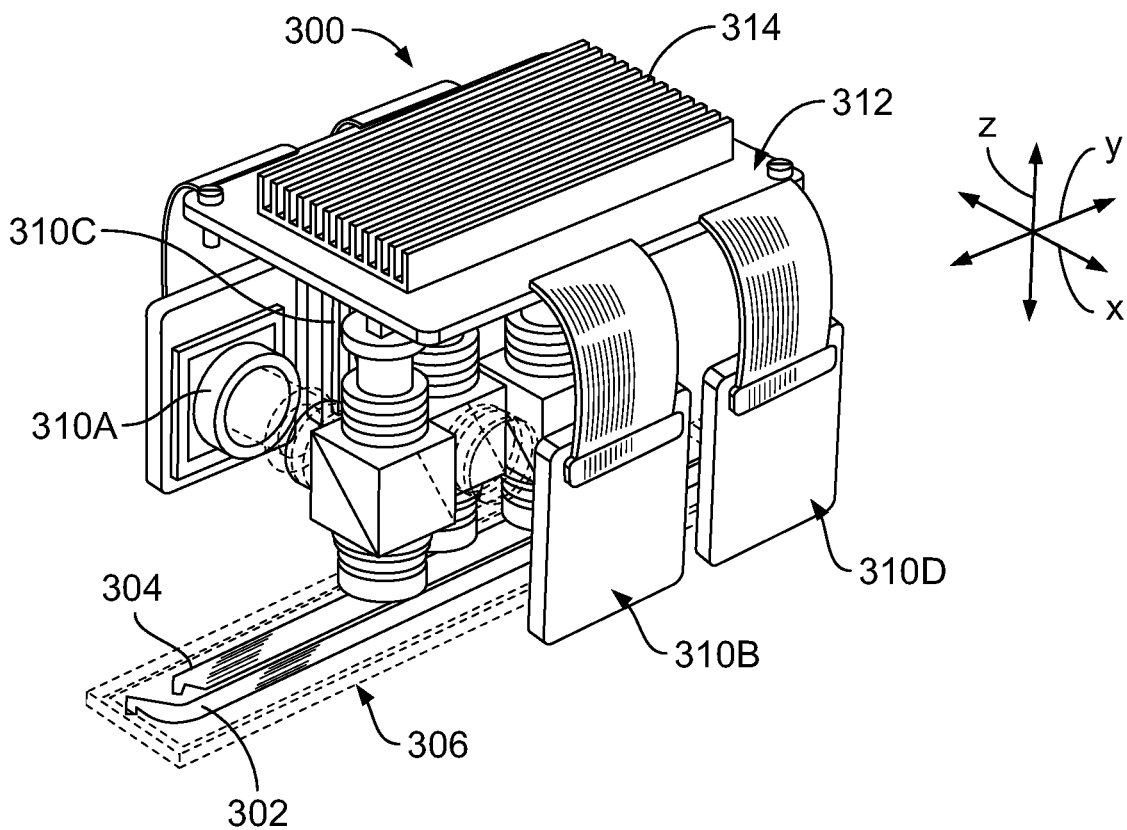
FIG. 6 shows an arrangement of four microfluorometers in relation to a flow cell having two channels.

FIG. 6 shows an exemplary arrangement of four microfluorometers in a single read head or carriage 300. The four microfluorometers are arranged in a staggered layout with respect to first and second channels 302 and 304 of a flow cell 306. In the arrangement shown, two of the microfluorometers (corresponding to detectors 310A and 310C) are configured to image separate regions of the first channel 302 and the other two microfluorometers (corresponding to detectors 310B and 310D) are configured to image separate regions of the second channel 304. As shown, the microfluorometers (corresponding to detectors 310A and 310C) are staggered with respect to the microfluorometers (corresponding to detectors 310B and 310D) in the x dimension such that the two pairs of microfluorometers can detect the adjacent first and second channels 302 and 304 respectively. The microfluorometers each have an orthogonal emission and excitation path with the radiation sources 312 positioned on the same side of the read head, opposite the flow cell 306. Two of the detectors 310A and 310C are positioned on a first side of the read head and the other two detectors 310B and 310D are positioned on the opposite side, both sides being orthogonal to the side where the excitation sources are positioned. In the exemplary embodiment shown in FIG. 6 the four radiation sources are in thermal contact with a single large heat sink 314. A single large heat sink provides a greater degree of heat dissipation than many configurations that use an individual heat sink for each radiation source. However, if desired individual radiation sources can be thermally coupled to individual heat sinks. An advantage of the arrangement of microfluorometers shown in FIG. 6 is the provision of a compact read head. Similar advantages can be derived for embodiments where the relative positions of the excitation source and detector in each microfluorometer are exchanged, The read head 300 shown in FIG. 6 is positioned to scan in the y dimension. The y dimension is parallel to the length of the flow cell 306 such that movement of the read head 300 in a scanning operation will result in imaging of areas along the length of the flow cell 306. The detectors 310A-310D are positioned on opposite sides of the read head 300, and on opposing sides of the flow cell 306, the sides of the flow cell running along the scan direction. The orientation of the read head 300 with respect to the flow cell 306 and scan direction is exemplary only and other orientations may be used.

A microfluorometer, or read head having several microfluorometers, can be positioned above a flow cell (with respect to gravity's arrow) as exemplified for several embodiments set forth herein. However, it is also possible to position a microfluorometer, or a read head, underneath a flow cell. Accordingly a flow cell can be transparent on the top side, bottom side or both sides with respect to the wavelengths of excitation and emission radiation used. Indeed, in some embodiments it may be desirable to position microfluorometers on both sides of a flow cell or to position read heads on both sides of a flow cell. Other orientations with respect to gravity are also possible, including for example a side to side orientation between a flow cell and microfluorometer (or read head).

A microfluorometer or read head can be configured to detect the two opposing, inner surfaces of a flow cell from a single side of the flow cell. For example, the microfluorometer or read head can employ an optical compensator that is inserted and removed to detect alternative surfaces of the flow cell. Exemplary methods and apparatus for detecting opposing inner surfaces of a flow cell such as the use of optical compensators are described in U.S. Pat. No. 8,039,817, which is incorporated herein by reference in its entirety. A compensator is optional, for example, depending upon the NA and/or optical resolution of the apparatus.

Figure 7:
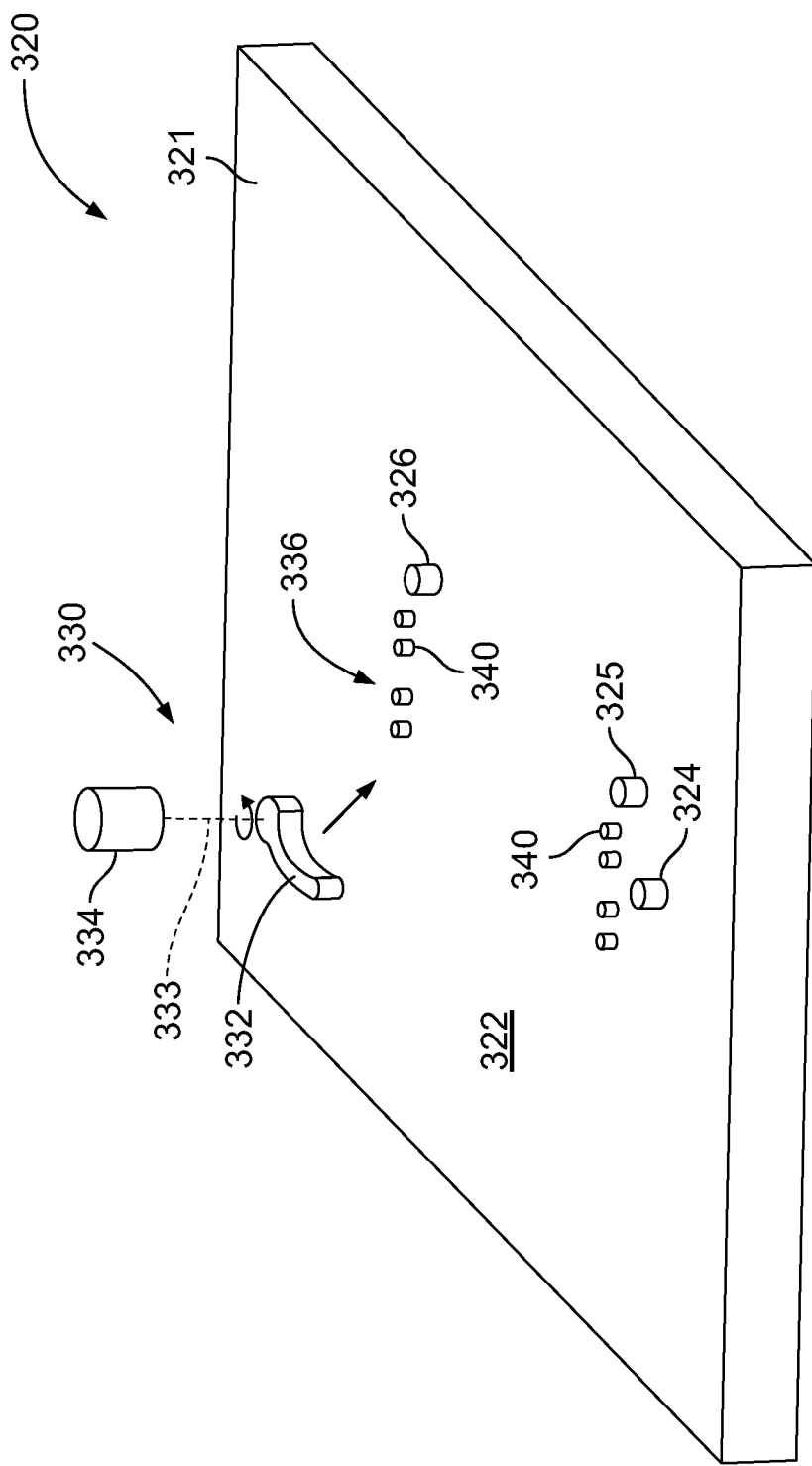
FIG. 7 is a perspective view of a portion of a system stage in accordance with an embodiment.
Figure 8:
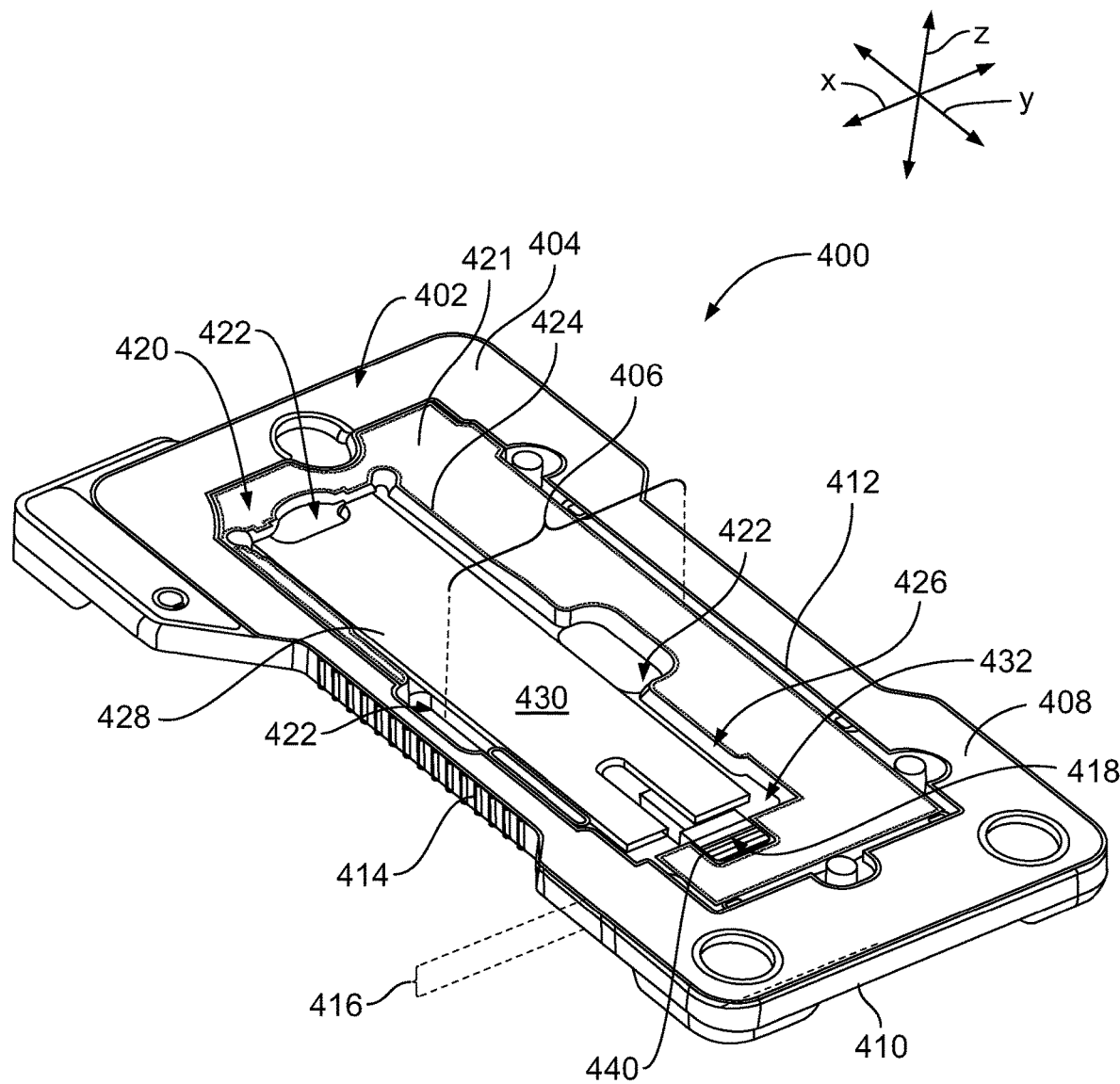
FIG. 8 is a perspective view of a carrier assembly formed in accordance with an embodiment.
Figure 12:
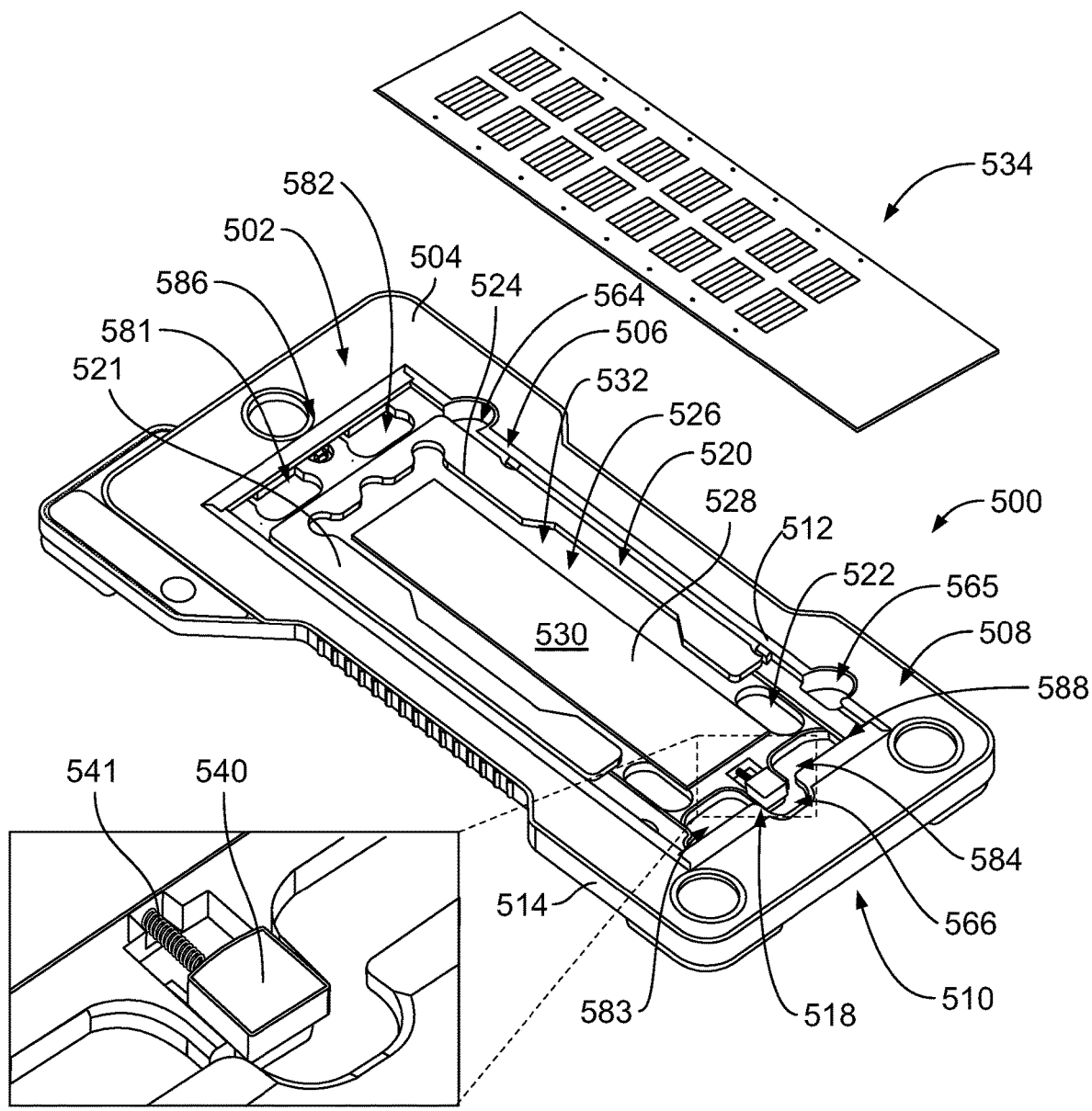
FIG. 12 is a perspective view of a carrier assembly formed in accordance with an embodiment.

FIG. 7 is a perspective view of a portion of a system stage 320 that is configured to receive a carrier assembly, such as the carrier assemblies 400 and 500 (FIGS. 8 and 12, respectively). The system stage 320 includes a stage body or platform 321 having a base surface 322 and a plurality of datums 324-326 that are positioned along the base surface 322. The datums 324-326 have fixed positions with respect to the base surface 322. In FIG. 7, the stage body 321 is block-shaped, but it should be understood that various shapes may be used. The base surface 322 is shaped to interface with a substrate and/or a carrier assembly. For example, at least a portion of the base surface 322 may be planar for interfacing with a flow cell. In some embodiments, the base surface 322 is configured to transfer thermal energy toward or away from the substrate of the carrier assembly. More specifically, the base surface 322 may be thermally coupled to a thermocycler. By way of example, when a flow cell is held by the carrier assembly and positioned on the base surface 322, the base surface 322 may conduct heat toward or absorb heat from the flow cell. In the illustrated embodiment, the base surface 322 that interfaces with the carrier assembly is planar. In other embodiments, however, the base surface 322 may be non-planar. For example, the base surface 322 may be shaped to complement a shape of the carrier assembly.

The datums 324-326 are configured to provide fixed reference points or surfaces that engage a substrate for holding the substrate in a fixed position relative to the optical system or, more specifically, the objective lens. In the illustrated embodiment, the datums 324-326 are cylindrical projections (e.g., posts) that extend away from the base surface 322, but the datums 324-326 may have other shapes in alternative embodiments. The positions of the datums 324-326 relative to one another and the base surface 322 may be based on the design of the carrier assembly, a shape of the substrate (e.g., a flow cell), and/or a shape of an adapter plate.

Also shown, the system stage 320 (or the docking system) may include an alignment mechanism 330 that is configured to engage the carrier assembly and/or substrate. In the illustrated embodiment, the alignment mechanism 330 includes a movable arm 332 that is configured to rotate about an axis 333. The movable arm 332 is operably connected to a motor 334 that is configured to drive the movable arm 332. The datums 324-326 and the movable arm 332 generally define a carrier-receiving area 336 of the base surface 322 therebetween. The carrier-receiving area 336 is configured to have the carrier assembly positioned thereon. When the carrier assembly is positioned on the carrier-receiving area 336, the motor 334 may drive the movable arm 332 toward the carrier assembly. The movable arm 332 may engage the carrier assembly and push the carrier assembly toward the datums 324-326.

In the illustrated embodiment, the movable arm 332 is rotated. In other embodiments, however, the movable arm 332 may be moved in other manners. For example, the movable arm 332 may be moved in a linear manner. In some embodiments, a single stroke that moves the movable arm 332 to engage the carrier assembly may include movement in multiple directions. For instance, the movable arm 332 may initially move in a first linear direction and then move in a second linear direction or rotate in another direction. In other embodiments, more than one alignment mechanism may be used. Moreover, alternative methods may also be used to hold the carrier assembly at a designated position. For example, pneumatic pumps may use gas (e.g., ambient air) to push or pull the carrier assembly in a designated manner.

Also shown in FIG. 7, the system stage 320 may include a plurality of manifold ports 340. The manifold ports 340 are configured to align with ports of a substrate, such as the ports of a flow cell. Fluid may be provided or drawn through the manifold ports 340.

FIG. 8 is a perspective view of a carrier assembly 400 in accordance with one embodiment. The carrier assembly 400 is configured to hold samples during imaging operations in which optical signals from a substrate are detected. The carrier assembly 400 may be used with an assay system, such as the assay system 100 of FIG. 1, and be positioned on a system stage, such as the system stage 320 (FIG. 7). The carrier assembly 400 includes a support frame 402. The support frame 402 includes a frame body 404 having first and second body sides 408, 410. The first body side 408 is configured to face an objective lens of an optical system, such as the objective lens 256. The second body side 410 is configured to interface with a system stage, such as the system stage 320 (FIG. 7).

The support frame 402 may define a sample region 406. In some embodiments, the sample region 406 includes an adapter plate 420. In other embodiments, the sample region 406 includes an open window or one or more thru-holes that extend entirely between the first and second body sides 408, 410. In some embodiments, the sample region 406 is a window that extends completely through the frame body 404 such that the window is accessible through either of the body sides 408, 410. The adapter plate 420 may be positioned within the window and coupled to the support frame 404. The adapter plate 420 may block an entirety or majority of the window. In some embodiments, the adapter plate 420 and the support frame 420 form one continuous structure. In other embodiments, the adapter plate 420 is removably coupled to the support frame 420. In alternative embodiments, the adapter plate 420 is not a part of the carrier assembly 400. For example, during SBS protocols, the carrier assembly 400 may only include the support frame 402 having a flow cell positioned within the sample region 406. During microarray imaging protocols, the carrier assembly 400 may include the adapter plate 420 and an open-face substrate, such as a beadchip.

The frame body 404 also includes an inner frame edge 412 and an outer frame edge 414. In some embodiments, the inner frame edge 412 may define the sample region 406. The outer frame edge 414 defines a perimeter of the frame body 404 and is configured to engage alignment features of a docking system (not shown). The alignment features may include, for example, an alignment mechanism, such as the alignment mechanism 330 (FIG. 7). The frame body 404 has a thickness 416 that is measured between the first and second body sides 408, 410. The support frame 402 is configured to be positioned on the system stage and permit an objective lens to move alongside the support frame 402 along a designated path during an imaging operation. As used herein, an objective lens may "move" when the objective lens and/or the system stage is moved such that the object that is desired to be imaged is moved relative to the objective lens. In the illustrated embodiment, the thickness 416 is substantially uniform such that the frame body 404 is substantially planar. In other embodiments, the frame body 404 may include nonplanar features. The nonplanar features may be positioned outside of the designated path of the objective lens.

Also shown in FIG. 8, the adapter plate 420 has a plate body 421. The adapter plate 420 is positioned within the sample region 406. In the illustrated embodiment, the adapter plate 420 covers an entirety of the sample region 406, except for passages or thru-holes 422 of the adapter plate 420 and apertures 464, 465, 466. In some embodiments, at least a portion of the adapter plate 420 may extend alongside or engage the second body side 410. The plate body 421 includes an inner plate edge 424. The inner plate edge 424 defines a pocket 426 of the adapter plate 420. The plate body 421 may also include a substrate or chip platform 428 within the pocket 426. The chip platform 428 has a platform surface 430 that is configured to have a substrate positioned thereon. The plate body 421 also includes a recess 432. In the illustrated embodiment, the recess 432 surrounds a majority of the platform 428.

Also shown in FIG. 8, the carrier assembly 400 may include a holding mechanism 418. The holding mechanism 418 may be coupled to the adapter plate 420 and/or the frame body 404. The holding mechanism 418 is configured to engage a substrate located within the pocket 426 to hold the substrate in a fixed position in the pocket 426. The holding mechanism 418 includes a movable datum block 440. In an exemplary embodiment, the datum block 440 is spring-loaded such that the datum block 440 may be deflected or moved into a compressed state and then released to engage a substrate (not shown) within the pocket 426 and hold the substrate within the pocket 426.

Figure 9:
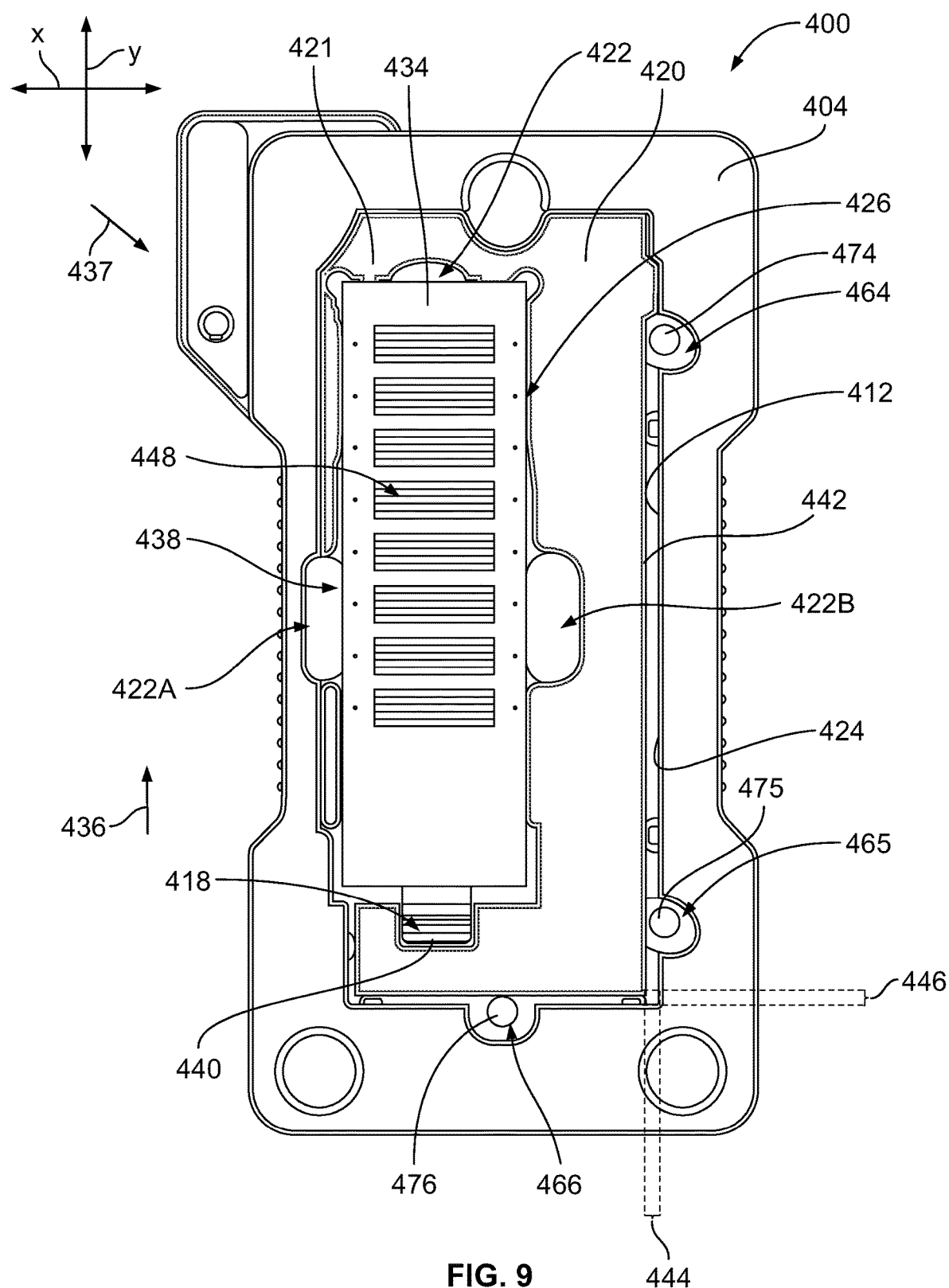
FIG. 9 is a plan view of the carrier assembly of FIG. 8 having a substrate positioned thereon.

FIG. 9 is a plan view of the carrier assembly 400 having a substrate 434 positioned within the pocket 426 of the adapter plate 420. The substrate 434 is held by the holding mechanism 418. More specifically, the datum block 440 of the holding mechanism 418 applies a holding force 436 that presses a substrate edge 438 against the inner plate edge 424. The holding force 436 is applied in a direction parallel to the XY plane. Accordingly, the substrate 434 is held in a fixed position relative to the adapter plate 420. In other embodiments, the holding force 436 may be at least partially applied in a direction that is perpendicular the XY plane such that the substrate 434 is pressed against the adapter plate 420. For example, the substrate 434 may be pressed against the platform surface 430 (FIG. 8).

In some embodiments, the adapter plate 420 may be movable along the XY plane relative to the frame body 404. For example, the adapter plate 420 may include an outer plate edge 442 that is configured to face the inner frame edge 412. In some cases, the outer plate edge 442 may represent an outermost edge of the adapter plate 420. In other cases, however, the outer plate edge 442 is not the outermost edge of the adapter plate 420. For example, a portion of the plate body 421 may extend beneath the frame body 404 (as shown in FIG. 9) and alongside the body side 410 (FIG. 8). As shown in FIG. 9, the outer plate edge 442 and the inner frame edge 412 may be separated by a tolerance gap 444 and a tolerance gap 446. The tolerance gap 444 has a distance that is measured along the X axis, and the tolerance gap 446 is a distance that is measured along the Y axis.

In other embodiments, however, the adapter plate 420 may have a fixed position with respect to the frame body 404. In particular embodiments, the adapter plate 420 and the frame body 404 may be molded within a common mold such that the frame body 404 and the adapter plate 420 are part of unitary piece of material. Alternatively, the frame body 404 and the adapter plate 420 may be discrete components that are secured to each in fixed positions with respect to each other.

Also shown in FIG. 9, the passages 422 are positioned around the substrate edge 438. The passages 422 are at least partially defined between an edge of the adapter plate 420 and a portion of the substrate edge 438. The passages 422 are sized and shaped to permit a portion of an individual's digit (e.g., finger) to be inserted therein and engage the substrate edge 438 for loading or removing the substrate 434. The passages 422 of the adapter plate 420 are positioned such that an individual while gripping the substrate 434 may position the substrate 434 within the pocket 426. For example, the passage 422A may receive a tip of an index finger or thumb, and the passage 422B may receive a tip of a thumb or index finger when the substrate 434 is positioned within the pocket 426. During the positioning operation, the holding mechanism 418 may be activated are compressed to move the datum block 440 away from the pocket 426. As the substrate 434 is positioned within the pocket 426 or after the substrate 434 is positioned within the pocket 426, the datum block 440 may be released so that the datum block 440 may move back toward the substrate 434 and engage the substrate edge 438. As shown, the substrate 434 is an open-face substrate having a microarray 448 thereon. Other types of substrates 434 may be used in other embodiments.

Figure 10:
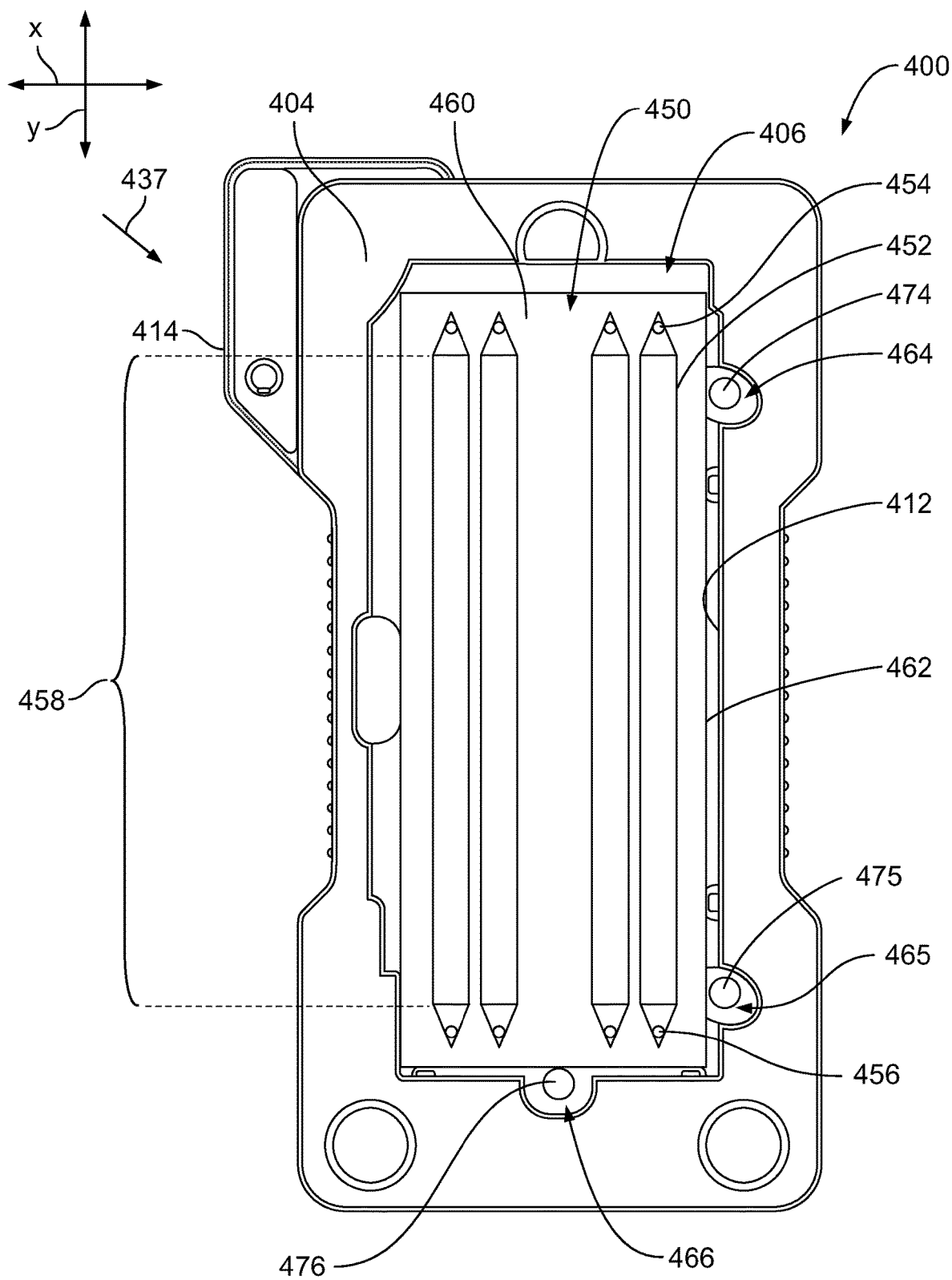
FIG. 10 is a plan view of the carrier assembly of FIG. 8 having another substrate positioned thereon.

FIG. 10 is a plan view of the carrier assembly 400 having a substrate 450 positioned within the sample region 406. The substrate 450 may be a flow cell having one or more flow channels. For example, in the illustrated embodiment, the flow cell 450 has four flow channels 452 formed within a flow cell body 460 of the flow cell 450. Each flow channel 452 has an imaging segment 458 that extends between a first port 454 and a second port 456. The first and second ports 454, 456 are openings or holes in the flow cell body 460. In the illustrated embodiment, the first port 454 is an inlet port and the second port 456 is an outlet port. In other embodiments, however, the first port 454 may be the outlet port and the second port 456 may be the inlet port. Also shown, the flow channels 452 are linear and the imaging segments 458 of the flow channels 452 extend parallel to each other. In other embodiments, however, the flow channels 452 may extend along nonlinear paths and/or may extend in nonparallel directions with respect to one another.

In the illustrated embodiment, the adapter plate 420 has been removed from the sample region 406. The frame body 404 or an alternative adapter plate (not shown) may include elements (not shown) that extend into the sample region 406 and provide resting surfaces for the flow cell 450 so that the frame body 404 prevents the flow cell 450 from going through the sample region 406. The flow cell body 460 includes an outer body edge 462. The outer body edge 462 is configured to engage at least a portion of the inner frame edge 412 of the frame body 404. In some embodiments, the flow cell 450 may be sized and shaped relative to the inner frame edge 412 such that the flow cell 450 may be movable along an XY plane within the sample region 406.

Referring to FIGS. 9 and 10, the frame body 404 includes apertures 464, 465, 466. In some embodiments in which the sample region 406 includes a window, the apertures 464-466 open to the window. The apertures 464-466 are sized and shaped to receive respective datums 474, 475, 476 of the system stage (not shown). The apertures 464-466 receive the respective datums 474-476 through the second body side 410. The datums 474-476 may be similar or identical to the datums 324-326 (FIG. 7). The datum 476 is configured to stop movement of the adapter plate 420 or, alternatively, the flow cell along the Y axis. The datums 474, 475 are configured to stop movement of the adapter plate 420 or, alternatively, the flow cell along the X axis. The apertures 464-466 are sized larger than the respective datums 474-476 to allow the frame body 404 to slide along the base surface during a positioning operation. Accordingly, the datums 474-476 are configured to align the flow cell 450 at a designated position or, alternatively, align the adapter plate 420 and, consequently, the substrate 434 at a designated position. In the designated position, the flow cell 450 may be positioned for imaging and for aligning the flow channels 452 with manifold ports of the system stage (not shown). Each of the first and second ports 454, 456 of the flow cell 450 may align with a corresponding manifold port. In the designated position, the substrate 434 is not fluidically coupled to any of the corresponding manifold ports. In some embodiments, the substrate 434 and/or the adapter plate 420 may seal the manifold ports.

To position the substrate 450 on the system stage, the substrate 450 may be positioned within the sample region 406 or window. The sample region 406 may be sized larger than the substrate 450 to allow some movement of the substrate 450 along the XY plane. The substrate 450 may engage one or more surfaces of the frame body 404 that prevent the substrate 450 from moving freely through the window 406. As the carrier assembly 400 is positioned on the system stage, the datums 474-476 may advance through the respective apertures 464-466. An alignment mechanism, such as the alignment mechanism 330 (FIG. 7), may be activated to move the frame body 404 along the XY plane. More specifically, a movable arm may engage the outer frame edge 414 and provide an alignment force 437 that causes the frame body 404 to move (e.g., shift) along the XY plane. As the frame body 404 moves along the XY plane, the substrate 450 engages the datums 474-476 and prevents the substrate 450 from moving further along the XY plane. The frame body 404 may move relative to the substrate 450 until the substrate 450 engages the inner frame edge 412 and prevents the frame body 404 from moving further. As such, the substrate 450 may have a designated location relative to an objective lens for detecting the optical signals.

Figure 11:
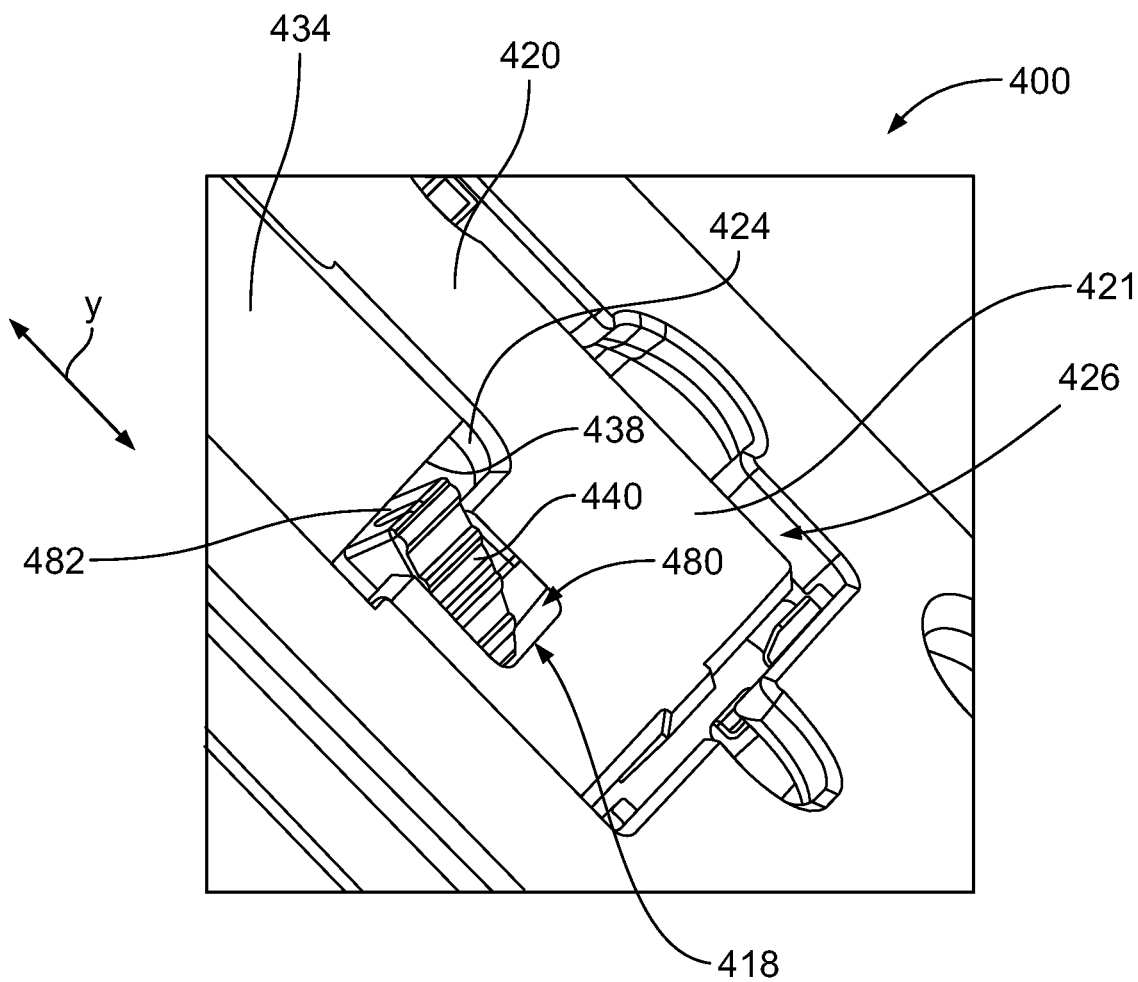
FIG. 11 is an enlarged view of a portion of the carrier assembly illustrating a holding mechanism in greater detail.

To position the substrate 434 on the system stage, the adapter plate 420 may be positioned within the sample region 406 of the frame body 404. For example, the adapter plate 420 may be coupled to the second body side 410 (FIG. 8) such that a portion of the adapter plate 420 is disposed within the window 406. Prior to the adapter plate 420 being positioned within the sample region 406 or after the adapter plate 420 is positioned within the sample region 406, the substrate 434 may be loaded into the pocket 426. For example, FIG. 11 illustrates a portion of the carrier assembly 400 in which the substrate 434 is engaged with the datum block 440 and held within the pocket 426. The datum block 440 is positioned within a holding recess 480 that is defined, at least in part, by the inner plate edge 424. The datum block 440 includes an engagement surface 482 that extends into the pocket 426 and is configured to engage the substrate 434 therein. The datum block 440 is configured to move relative to the pocket 426 or the adapter plate 420 to allow the substrate 434 to be freely positioned within the pocket 426. For example, the datum block 440 may be pressed so that the engagement surface 482 is positioned within the plate body 421 and not within the pocket 426. As the substrate 434 is loaded into the pocket 426 or after the substrate 434 is loaded into the pocket 426, the datum block 440 may be released to allow the engagement surface 482 to engage the substrate edge 438. The engagement surface 482 may be shaped so that the datum block 440 urges the substrate 434 along the Y axis. The substrate 434 may be held between the datum block 440 and a portion of the inner plate edge 424. In an exemplary embodiment, the holding mechanism 418 includes a spring that holds the datum block 440 in the biased position. However, alternative holding mechanisms may be used.

Returning to FIG. 9, with the substrate 434 positioned within and held by the adapter plate 420, the carrier assembly 400 may be loaded onto the system stage. As the carrier assembly 400 is positioned on the system stage, the datums 474-476 may advance through the respective apertures 464-466. As described above, the alignment mechanism may be activated to move the frame body 404 along the XY plane. As the frame body 404 moves along the XY plane, the adapter plate 420 engages the datums 474-476 that prevent the adapter plate 420 from moving further along the XY plane. In some embodiments, the frame body 404 may move relative to the adapter plate 420 until the adapter plate 420 engages the inner frame edge 412 and prevents the frame body 404 from moving further. As such, the adapter plate 420 may have a fixed position relative to the objective lens and, consequently, the substrate 434 may have a designated location relative to the objective lens for detecting the optical signals.

As described herein, in alternative embodiments, the adapter plate 420 may have a fixed position relative to the frame body 404. For example, the adapter plate 420 may be removably secured to the frame body 404 such that the adapter plate 420 does not shift or move relative to the frame body 404. Alternatively, the frame body 404 and the adapter plate 420 may be part of the same unitary structure.

FIG. 12 is a perspective view of a carrier assembly 500 in accordance with an embodiment. The carrier assembly 500 may include features and elements that are similar or identical to the carrier assembly 400 (FIG. 8). The carrier assembly 500 may be used with an assay system, such as the assay system 100 of FIG. 1. The carrier assembly 500 includes a support frame 502. The support frame 502 includes a frame body 504 that defines a sample region 506. The frame body 504 includes first and second body sides 508, 510. In the illustrated embodiment, the sample region 506 forms a pocket or space for receiving a substrate. Also shown, an inner frame edge 512 of the frame body 504 defines apertures 564, 565, and 566 of the frame body 504 that open to the sample region 506. The apertures 564-566 are sized and shaped to receive datums (not shown) for aligning a flow cell during a positioning operation.

The frame body 504 includes the inner frame edge 512 and also an outer frame edge 514. The inner frame edge 512 may define the sample region 506. The outer frame edge 514 defines a perimeter of the frame body 504 and is configured to engage alignment features (not shown) of the optical system. The carrier assembly 500 includes an adapter plate 520 having a plate body 521. The adapter plate 520 is positioned within the sample region 506 in the illustrated embodiment. The adapter plate 520 spans the entire sample region 506, except for passages or thru-holes 522 and the apertures 564-566.

In some embodiments, the adapter plate 520 and the support frame 502 are discrete components. In such embodiments, at least a portion of the adapter plate 520 may extend alongside or engage the second body side 510 of the frame body 504. The plate body 521 includes an inner plate edge 524. The inner plate edge 524 defines a pocket 526 of the adapter plate 520. The plate body 521 also includes a substrate or chip platform 528 within the pocket 526. The chip platform 528 includes a platform surface 530 that is configured to have a substrate 534 positioned thereon. The plate body 521 also includes a recess 532.

Also shown in FIG. 12, the adapter plate 520 includes a holding mechanism 518 that is coupled to the plate body 521. The holding mechanism 518 is configured to engage the substrate 534 when the substrate 534 is positioned within the pocket 526 to hold the substrate 534 in a fixed position relative to the adapter plate 520. The holding mechanism 518 includes a movable datum block 540 that is operably coupled to a spring 541. The spring 541 is configured to urge the substrate 534 along the Y axis to hold the substrate 534 between the datum block 540 and the inner plate edge 524. In the illustrated embodiment, the datum block 540 may be pulled away from the pocket 526 to permit the substrate 534 to be positioned therein.

In some embodiments, the adapter plate 520 may be coupled to the frame body 504 when the substrate 534 is positioned on the adapter plate 520 and when a flow cell, which may be similar to the substrate 450 (FIG. 10), is positioned on the adapter plate 520. For example, the adapter plate 520 may include fluid openings 581, 582, 583, and 584. The fluid openings 581, 582 are located at one end 586 of the adapter plate 520 and the fluid openings 583, 584 are located at the opposite end 588 of the adapter plate 520. The fluid openings 583, 584 are located on opposite sides of the holding mechanism 518. The fluid openings 581-584 permit manifold ports (not shown) of a manifold (or system stage) to access a flow cell. For example, nozzles may extend through the fluid openings 581-584 and engage ports of the flow cell.

Figure 13:
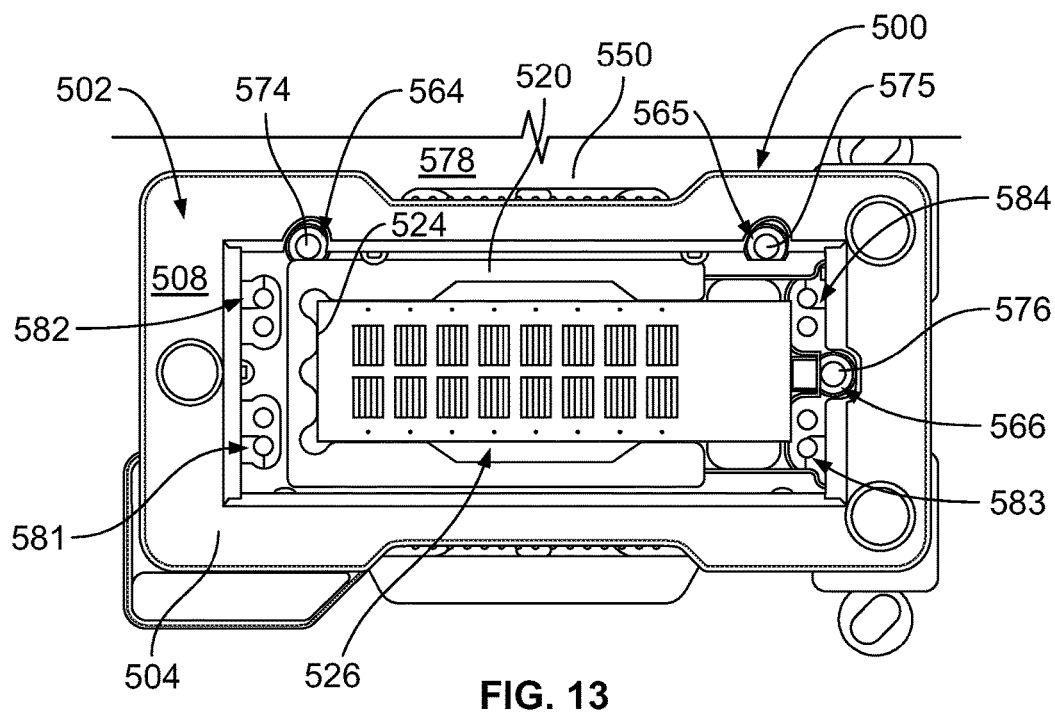
FIG. 13 is a plan view of the carrier assembly of FIG. 12 positioned on a system stage.

FIG. 13 is a plan view of the carrier assembly 500 positioned on a system stage 550. The system stage 550 includes a plurality of datums 574-576 projecting from a base surface 578 of the system stage 550. The second body side 510 (FIG. 12) of the support frame 502 engages the base surface 578. The first body side 508 faces an objective lens (not shown) during an imaging operation. The apertures 564-566 of the support frame 502 open to the second body side 510 and extend from the second body side 510 toward the first body side 508. In the illustrated embodiment, the apertures 564-566 extend completely through the support frame 502. However, in other embodiments, the apertures 564-566 may be recesses that extend only partially into the support frame 502. The apertures 564-566 receive the respective datums 574-576.

In some embodiments, the adapter plate 520 is movable (e.g., slidable) with respect to the frame body 504. In other embodiments, the adapter plate 520 has a fixed position relative to the frame body 504. The fluid openings may also receive nozzles of the manifold when the carrier assembly 500 is positioned on the system stage. As shown, the pocket 526 is centrally located such that the fluid openings 581, 582 and the fluid openings 583, 584 are located on opposite ends of the pocket 526. The pocket 426 (FIG. 8), however, is not centrally located. Instead, the pocket 426 is located closer to one side than another side. The pocket 426 is located further away from the corresponding datums than the pocket 526. Also shown in FIG. 13, the datum 576 may engage the datum block 540. In an exemplary embodiment, the datum 576 may facilitate pressing the datum block 540 into the substrate 534. The substrate 534 may be held between the datum block 540 and one or more portions of the inner plate edge 524.

Figure 14A:
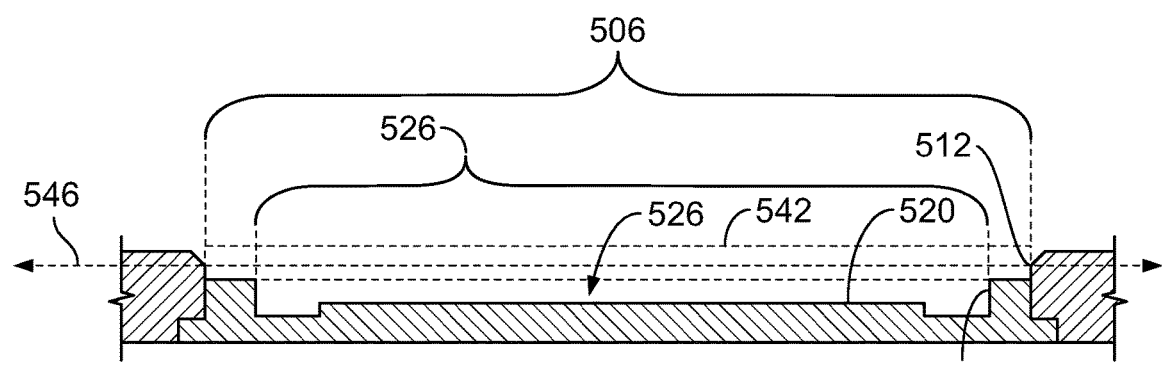
FIG. 14A is a cross-section of the carrier assembly of FIG. 12.

FIG. 14A is a cross-section of a portion of the carrier assembly 500 illustrating the sample region 506 and the pocket 526 in greater detail. As shown, the adapter plate 520 is coupled to the support frame 502 and positioned within the sample region 506. The inner frame edge 512 defines a substrate-receiving recess 542 (indicated by a dashed rectangular box) that is positioned above the adapter plate 520 and above the pocket 526. The substrate-receiving recess 542 is sized and shaped to receive a first planar substrate, such as the flow cell 450. The inner plate edge 524 defines the pocket 526. The pocket 526 is sized and shaped to receive the substrate 534, which is also planar and is sized smaller than the first planar substrate. The pocket 526 exists at least partially below the substrate-receiving recess 542. In some embodiments, the pocket 526 at least one of coincides with a receiving plane 546 that intersects the inner frame edge 512 or is positioned below the receiving plane 546. In the illustrated embodiment, the pocket 526 is positioned below the receiving plane 546. The receiving plane 546 extends parallel to an XY plane formed by the X and Y axes. Although the pocket 526 is located below the receiving plane 546, it should be understood that a portion of the substrate 534 may be located within the substrate-receiving recess 542 during the imaging operation.

Figure 14B:
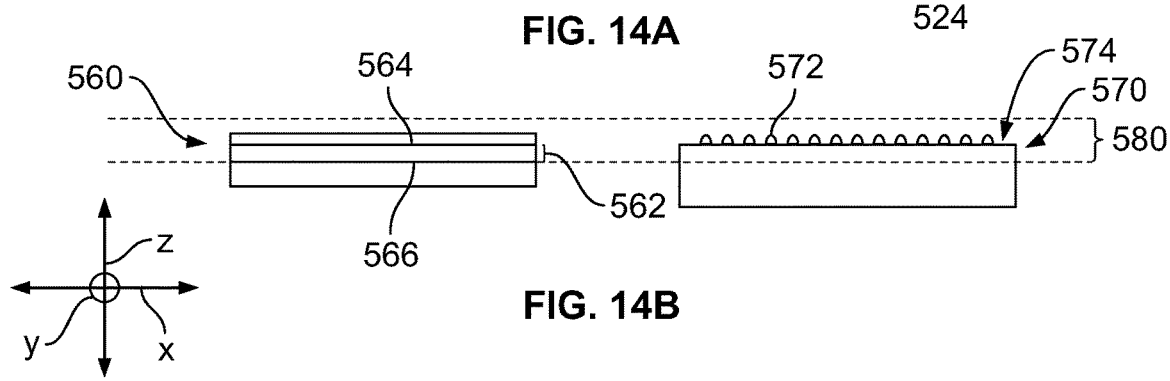
FIG. 14B illustrates a flow cell and an open-face substrate side-by-side.

FIG. 14B illustrates a flow cell 560 and an open-face substrate 570 side-by-side. The flow cell 560 has a flow channel 562 defined between two interior channel surfaces 564, 566. In the illustrated embodiment, the open-face substrate 570 includes a microarray of features 572, such as beads, in which each feature has a designated address (among the features in the microarray) and a designated chemical substance (e.g., nucleic acid). A table or database may correlate each address to a corresponding chemical substance. The features 572 are located along a substrate surface 574.

The carrier assemblies set forth herein are configured to hold different types of substrates, such as the flow cell 560 and the open-face substrate 570, so that the desired surface or area to be imaged is located within an imaging zone 580 of the optical system. The imaging zone 580 may represent a generally planar volume that the optical system is capable of focusing within. The general planar volume may have an X dimension, Y-dimension, and Z-dimension. The X and Y dimensions may be several millimeters or more. The Z-dimension may be within 1000 microns or less. More specifically, the Z-dimension may be 900 microns or less, 800 microns or less, 700 microns or less, 600 microns or less, or 500 microns or less. In particular embodiments, the Z-dimension may be 400 microns or less, 300 microns or less, or 200 microns or less. In more particular embodiments, the Z-dimension may be 90 microns or less, 80 microns or less, 70 microns or less, or 60 microns or less. In yet more particular embodiments, the Z-dimension may be 50 microns or less, 40 microns or less, 30 microns or less, 20 microns or less, or 10 microns or less.

In some embodiments, the substrate surface 574 and at least one of the interior channel surfaces 564, 566 are capable of being positioned by the carrier assembly (not shown) within the imaging zone 580. The carrier assembly may be similar or identical to any of the carrier assemblies described herein. Accordingly, each of the open-face substrate 570 and the flow cell 560 may be examined by the optical system. As shown in FIG. 14B, the substrate surface 574 and the channel surface 564 are co-planar. In other embodiments, the substrate surface 574 may be co-planar with the channel surface 566. In other embodiments, the substrate surface 574 may not be co-planar with either channel surface. The substrate surface 574 may be offset along the Z-axis with the corresponding channel surface by designated maximum amount $\Delta Z$. The maximum amount $\Delta Z$ may be, for example, 100 microns or less, 90 microns or less, 80 microns or less, 70 microns or less, 60 microns or less, 50 microns or less, 40 microns or less, 30 microns or less, 20 microns or less, or 10 microns or less. However, the maximum amount $\Delta Z$ of the offset may be greater in other embodiments. In the illustrated embodiment, the open-face substrate 570 has a thickness that is greater than the thickness of the flow cell 560. In other embodiments, the thickness of the flow cell 560 may be greater than the thickness of the open-face substrate 570. In other embodiments, the thicknesses may be substantially equal.

Figures 15, 16:
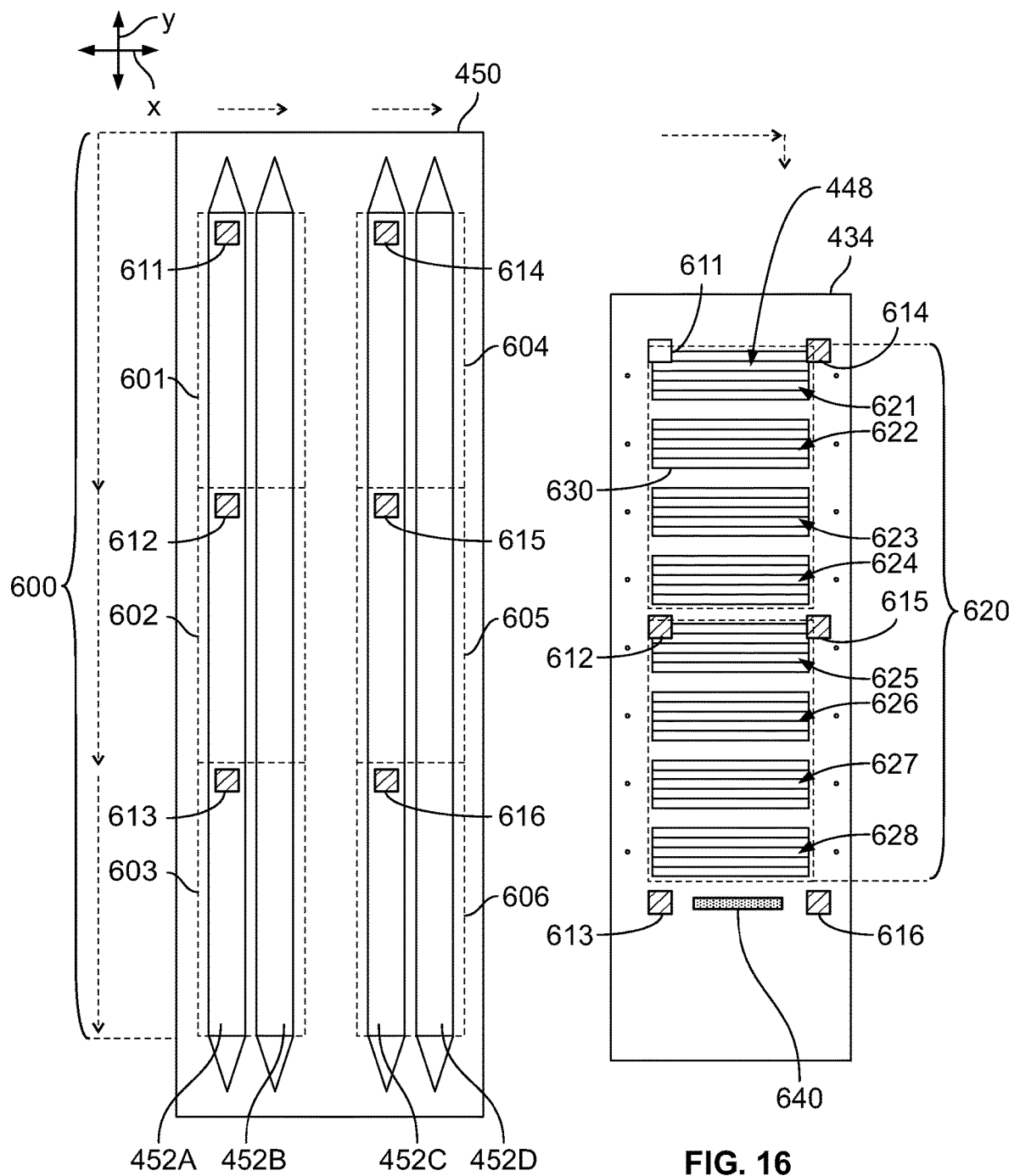
FIG. 15 illustrates an imaging zone of an optical system relative to the substrate of FIG. 10.
FIG. 16 illustrates an imaging zone of the optical system relative to the substrate of FIG. 9.

FIGS. 15 and 16 are plan views of the substrates 450, 434, respectively, which are hereinafter referred to as a flow cell and an open-face substrate, respectively. The flow cell 450 includes the four flow channels 452A, 452B, 452C, 452D that extend parallel to one another along a Y-axis. In alternative embodiments, more or fewer flow channels may be used. The flow channels 452A-452D are aligned such that each flow channel begins and ends at effectively the same axial locations along the Y-axis. The open-face substrate 434 includes the microarray 448. The microarray 448 includes a plurality of array sections 621-628 in which each section includes a plurality of feature stripes or lanes 630. In the illustrated embodiment, the microarray 448 includes eight (8) array sections in which each section has five (5) feature stripes. In other embodiments, however, more or fewer array sections may be used. In other embodiments, each array section may include more or fewer feature stripes. In the illustrated embodiment, the array sections are separated from each other. In other embodiments, the microarray 448 includes one continuous array without separate array sections.

FIGS. 15 and 16 also illustrate imaging zones 600, 620, respectively, which may be similar or identical to the imaging zone 580. The imaging zones 600, 620 represent the three-dimensional zone that optical signals may be detected from by the optical system from the flow cell 450 and the open-face substrate 434, respectively. Different assay protocols may be configured (e.g., programmed) to image the corresponding zones. In some embodiments, the imaging zone represents a sum total of the volume that may be scanned by an optical system for the corresponding substrate. In particular embodiments, the imaging zone 600 may completely overlap the imaging zone 620. In other embodiments, the imaging zones 600, 620 may include non-overlapping portions. The imaging zones 600, 620 are generally planar zones with a small Z-dimension. The optical system may include a read head or carriage (not shown) that is similar to the read head 300 (FIG. 6). The optical system may include six microfluorometers (not shown) having, among other things, six objective lenses (not shown). Each objective lens is configured to scan a corresponding sub-zone.

As described herein, one or more different types of substrates may be held within the same imaging zone of an optical system. For example, a first carrier assembly having a first type of substrate on a system stage may be replaced with a second carrier assembly on the system stage. The second carrier assembly may have a second type of substrate. Each of the substrates of the first and second carrier assemblies may be held such that the respective samples are positioned within the same imaging zone. Accordingly, although the following describes imaging zones 600, 620 separately, it should be understood that the imaging zones may at least partially overlap each other. For example, the sample (e.g., microarray of features) along a second substrate may be positioned within the same imaging zone that is used for a different first substrate (e.g., flow cell).

Each objective lens of the microfluorometers may have a field of view (FOV) that corresponds to an area that may be imaged or captured by the objective lens in a single image. FIGS. 15 and 16 illustrate six FOVs 611-616. The optical system is configured to move the objective lenses relative to the corresponding substrate to obtain a plurality of images. The optical system is a point-and-shoot optical system in which several distinct images are captured to cover the entire imaging zone. In other embodiments, the optical system may be a line-scanning or point-scanning optical system. In FIG. 15, each of the FOVs 611-616 is configured to be moved along a portion of a first flow channel and then along a portion of a second flow channel. After the imaging operation, all four flow channels may be completely (or near completely) imaged. In FIG. 16, only two of the FOVs 611, 612 move along the microarray to obtain a plurality of images of the microarray. In some embodiments, one or more FOVs that are not used to image the substrate may be used to image an identification code 640 (e.g., bar code) that identifies the type of substrate.

By way of example, during a first imaging operation, the read head may be moved along the flow cell 450. As the read head is moved relative to the system stage, each of the objective lenses may detect optical signals from the corresponding FOV. As shown in FIG. 15, the imaging zone 600 is formed from six separate sub-zones 601-606. Each of the sub-zones 601-606 represents a portion of the imaging zone 600 that may be imaged through one of the corresponding FOVs. For example, the read head may be moved along the Y-axis. The FOVs 611-613 may obtain a plurality of images of the flow channel 452A, and the FOVs 614-616 may obtain a plurality of images of the flow channel 452C. In some embodiments, the read head may intermittently pause so that the flow cell 450 and the read head have substantially fixed positions with respect to each other as the images are obtained. In other embodiments, the read head may not pause and may continuously move along the flow cell 450. Due to the number of microfluorometers and positions of the corresponding FOVs, the entire length of the flow channels 452A and 452C may be imaged after the read head has moved about ⅓ of the length of the flow channels. Optical signals emitting from the flow cell may be detected by the corresponding image sensors (e.g., CMOS imagers). According, two flow channels may be imaged concurrently or simultaneously.

In some embodiments, the FOVs 611-616 are dimensioned such that a width of the FOVs along the X-axis is smaller than a width of the corresponding flow channel. In such embodiments, the imaging of the flow channels 452A, 452C may be repeated. For example, the optical system may move the FOVs 611-616 an incremental amount along the X-axis such that the FOVs remain within the flow channels 452A, 452C, but are located at a different X position. The FOVs 611-616 may then be moved again along the Y-axis to image another strip of the flow channels 452A, 452C. The process of incrementally moving the FOVs along the X-axis and imaging along the Y-axis may be repeated a number of times until the entire flow channels 452A, 452C are imaged. In other embodiments, the FOVs 611-616 are large enough to capture an entire width of the flow channels 452A, 452C such that only one stage of moving the FOVs 611-616 along the Y-axis is necessary.

The read head may then be moved along the X-axis so that the FOVs 611-613 are positioned for imaging the flow channel 452B and the FOVs 614-616 are positioned for imaging the flow channel 452D. The read head may then be moved along the Y-axis. The FOVs 611-613 may obtain a plurality of images of the flow channel 452B, and the FOVs 614-616 may obtain a plurality of images of the flow channel 452D. In some embodiments, the read head may briefly pause so that the flow cell 450 and the read head have substantially fixed positions with respect to each other as the images are obtained. Due to the number of microfluorometers and positions of the corresponding FOVs, each of the flow channels 452B and 452D may be imaged after the read head has moved about ⅓ of the length of the flow channels. As discussed above, the FOVs may be moved incrementally along the X-axis and the flow channels 452B, 452D may be imaged again until the entire desired portions of the flow channels are imaged.

Accordingly, during a first imaging protocol in which the read head detects optical signals from the flow cell, the read head is configured to move along the Y-axis a designated distance (e.g., about ⅓ the length of the flow channels) and a short distance along the X-axis to optionally re-position the FOVs within the same flow channel and then position the FOVs in an adjacent flow channel.

Image data obtained from the flow cell 450 may be transmitted to and/or processed by a detection data analysis module of the assay system. Optionally, the assay system may then detect optical signals from a different surface of the flow cell. For example, optical signals may be detected from a top surface of a flow channel during a first imaging session and detected from a bottom surface during a second imaging session. In some embodiments, the optical system (or optical train) may be modified between the first and second imaging sessions.

During a second imaging operation, the read head may be scanned along the open-face substrate 434. Unlike the first imaging operation, the second imaging operation may only utilize two of the microfluorometers for detecting optical signals from chemical substances. In the illustrated embodiment, only the microfluorometer associated with the FOV 611 and the microfluorometer associated with the FOV 612 are utilized to image the microarray 448. More specifically, the FOV 611 may be moved along each of the feature stripes 630 for each of the array sections 621-624, and the FOV 612 may be moved along each of the feature stripes 630 for each of the array sections 625-628. As one feature stripe 630 is imaged through the FOV 611, another feature stripe 630 is imaged through the FOV 612. Thus, two feature stripes 630 may be imaged concurrently or simultaneously.

As indicated by the hatching of FOVs 613-616, the microfluorometers associated with the FOVs 613-616 do not capture images of the microarray 448. In some embodiments, however, one or more FOVs may capture an image (or images) of the identification code 640. For example, the FOV 613 may image the identification code 640 as the FOVs 611, 612 capture images of the microarray 448. The images of the identification code 640 may be analyzed by the system to identify the type of microarray. In some embodiments, the identification code 640 may include information about the microarray. For example, the identification code 640 may identify the addresses and identities of the features within the microarray. In other embodiments, the identification code 640 may be used to determine the addresses and identities of the features within the microarray by using, for example, a database. Although FIG. 16 shows the identification code 640 at one particular position, the identification code 640 may have other positions. For example, the identification code 640 may be positioned closer to the imaging zone 620 along the array section 628. Alternatively, the identification code 640 may be positioned closer to the bottom edge of the open-face substrate 434.

Image data obtained from the open-face substrate 434 may be transmitted to and/or processed by a detection data analysis module of the assay system. In either of the first and second imaging operations, the image data may be digitally stitched together as described below. Alternatively, the image data may not be stitched together. For example, each sub-zone may be analyzed as a separate image.

Figure 17:
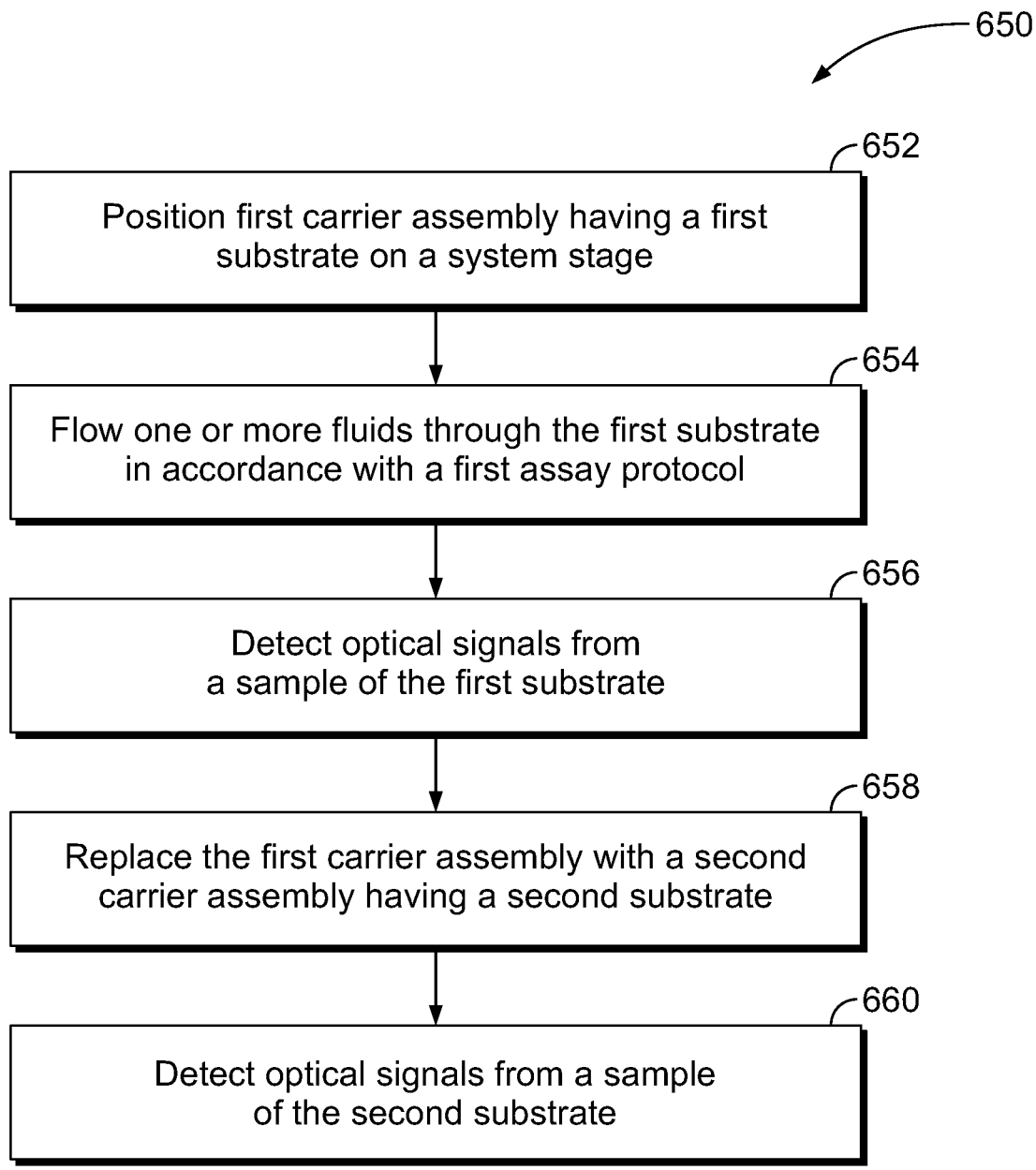
FIG. 17 is a flow-chart illustrating a method in accordance with an embodiment.

FIG. 17 is a flow-chart illustrating a 650 method in accordance with an embodiment. The method 650 may be performed or executed, at least in part, by an assay system, such as the assay system 100 (FIG. 1). The method 650 includes positioning, at 652, a first carrier assembly on a system stage. The system stage may be similar or identical to the system stage 320. The carrier assembly may include a support frame having an inner frame edge that defines a window of the support frame. The first carrier assembly may include a first substrate that is positioned within the window and surrounded by the inner frame edge. The first substrate has a sample thereon that is positioned within an imaging zone of an optical system.

By way of example, the first substrate may be a flow cell. If the first substrate is a flow cell, the method 650 may also include flowing, at 654, one or more fluids through a flow channel (or multiple flow channels) of the flow cell. The flowing, at 654, may be performed in accordance with a predetermined sequence in which, for example, a first liquid is provided through the flow channel, followed by a second liquid, followed by a third liquid, and followed by a fourth liquid. The liquids may be configured for performing a predetermined assay protocol, such as an SBS assay protocol. For example, the first liquid may be a solution that includes fluorescently-labeled nucleotides, the second liquid may be a wash solution (e.g., buffer solution), the third liquid may be a cleaving solution, and the fourth liquid may be another wash solution.

At 656, optical signals from the sample of the first substrate may be detected using an optical system. In some embodiments, the detecting, at 656, may include illuminating the first substrate with an excitation light or excitation lights. For example, the sample on the first substrate may include fluorescent labels that provide light emissions of a predetermined wavelength when excited by excitation light of a predetermined wavelength. For embodiments in which the first substrate is a flow cell, the detecting, at 656, may be sequenced with the flowing, at 654, of one or more fluids. For example, during an SBS assay protocol, fluorescently-labeled bases are sequentially added to the nucleic acids of each cluster. After each incorporation event, the sample may be excited and optical signals may be detected from the sample.

The optical system may capture a series of images of each flow channel using one or more microfluorometers in accordance with a first imaging protocol. The first assay protocol may include the first imaging protocol. The first assay protocol may be stored as a set of instructions within one or more modules (e.g., memory). The first imaging protocol includes a sequence of steps for moving the first substrate with respect to the optical system and capturing designated portions of the imaging zone. For example, the sequence may include imaging a series of images along one strip of the flow channel and, subsequently, a series of images along an adjacent strip of the same flow channel as described herein. The sequence may also include moving the FOVs to another flow channel and repeating the process for capturing images from the other flow channel. As described above, the optical system may include a read head having a plurality of microfluorometers.

The method 650 may also include replacing, at 658, the first carrier assembly on the system stage with a second carrier assembly on the system stage. The second carrier assembly may include the support frame and an adapter plate that is held by the support frame. The second carrier assembly may have a second substrate held by the adapter plate that has a sample thereon. The second substrate may be, for example, an open-face substrate. The sample of the second substrate is positioned within the imaging zone of an optical system.

The replacing, at 658, may include replacing the entire first carrier assembly with an entirely new second carrier assembly. In some embodiments, however, the replacing, at 658, includes changing the configuration of the first carrier assembly such that the adapter plate is added to the support frame. In other words, the first and second carrier assemblies may use the same support frame, but the second carrier assembly may include an adapter plate coupled to the support frame. It should also be understood that replacing, at 658, may include removing the first carrier assembly on the system stage and positioning the second carrier assembly on the system stage within a short period of time (e.g., within minutes), but may also include removing the first carrier assembly on the system stage and positioning the second carrier assembly on the system stage after an extended period of time (e.g., days).

At 660, optical signals from the second substrate may be detected using the optical system. As described above, the detecting, at 660, may include exciting fluorescent labels of the sample and detecting the light emissions therefrom. The detecting, at 660, may include capturing a series of images of the second substrate using one or more microfluorometers in accordance with a second assay (or imaging) protocol. The second assay protocol is different from the first assay protocol. The second assay protocol may be stored as a set of instructions within one or more modules (e.g., memory). The second assay protocol includes a sequence of steps for moving the second substrate with respect to the optical system and capturing designated portions of the imaging zone. For example, the sequence may include imaging a series of images along one feature stripe of a microarray and, subsequently, a series of images along an adjacent feature stripe as described herein. After the optical signals from the second substrate are detected, second carrier assembly may be replaced, at 662, with a third carrier assembly. The third carrier assembly may or may not include the adapter plate and may or may not include a substrate that is similar to the substrate of the first carrier assembly or the substrate of the second carrier assembly.

Accordingly, the same assay system may be configured to carry out different imaging protocols for detecting optical signals from different types of substrates. The different imaging protocols may include different movements of the substrate relative to the objective lens or lenses. For embodiments that utilize more than one objective lens or microfluorometer, it is contemplated that the imaging protocols utilize a different number of available microfluorometers. For example, a first imaging protocol may utilize six microfluorometers of a total of six available microfluorometers. A second imaging protocol, however, may only utilize two of the available six microfluorometers.

In the first imaging protocol, the assay system may control an objective lens and/or system stage to image a first series of side-by-side discrete images along one axis (e.g., Y-axis) of a substrate surface, such as a channel surface of a flow cell. Optionally, the assay system may control the objective lens and/or system stage to move the objective lens along X-axis and image a second series of side-by-side discrete images along one axis (e.g., Y-axis) of the substrate surface. The second series may be adjacent to the first series such that the images of the first and second series are adjacent to each other. After the substrate surface is imaged, the assay system may control the objective lens and/or system stage to image a separate substrate surface in a similar manner. After the other substrate surface, the assay system may control the objective lens and/or system stage to flow reagents through the flow channel. The imaging protocol may then be repeated. The images may be analyzed to determine a characteristic or property of the sample. In particular embodiments, the first imaging protocol may be used during an SBS protocol. As described above, the first imaging protocol may include only one objective lens (or microfluorometer) or a plurality of objective lenses having predetermined locations with respect to one another.

In the second imaging protocol, the assay system may control the objective lens and/or system stage to image a different type of substrate. For example, the different type of substrate may include a microarray having a plurality of discrete sections. Optionally, each discrete section may include a plurality of discrete feature stripes. In the second imaging protocol, the assay system may control the objective lens and/or system stage to image a first series of side-by-side discrete images along one axis (e.g., X-axis) of the substrate surface. More specifically, the first series of discrete images may be of a first feature stripe of the microarray. The assay system may then control the objective lens and/or system stage to move the objective lens along the Y-axis to another feature stripe. A second series of side-by-side discrete images may be generated along the X-axis. The second series may be adjacent to the first series, although the first and second series may not abut each other.

FIGS. 18-21 illustrate a stitching operation in which images captured from adjacent areas of a substrate surface (e.g., substrate surface having a microarray) may be combined or stitched together to provide a complete representation of the substrate surface. The complete representation may be a data representation that provides a location (e.g., address or absolute coordinates) and signal value of each feature. Alternatively, the complete representation may be a combined image that comprises multiple images stitched together. The stitching operation may be used to form a data representation of, for example, the microarray 448 (FIG. 9). However, it is contemplated that the data representation may be of other microarrays, such as a random arrays or ordered arrays of nucleic acids clusters. The stitching operation is a method that may be executed by the assay system or another computing system within a commercially reasonable period of time. The stitching operation may be stored as a set of instructions within memory. The stitching operation may form part of an assay protocol, such as the second assay protocol described above.

Figure 18:
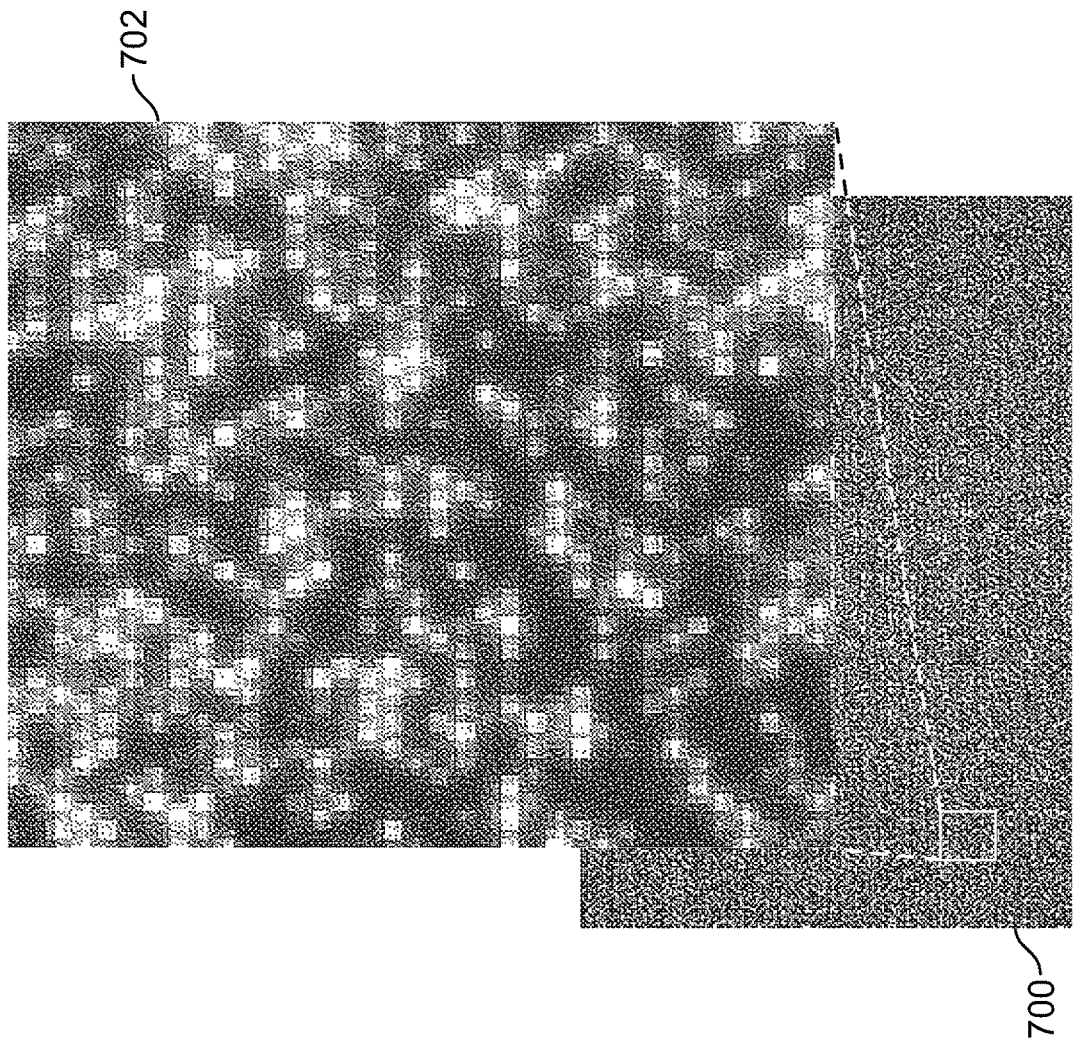
FIG. 18 is an image of a microarray in accordance with one embodiment.

FIG. 18 shows an image 700 in accordance with one embodiment. The image 700 may show, for example, a portion of a feature stripe of a microarray. FIG. 18 also illustrates a magnified section 702 of the image 700. The image 700 includes a dense array of pixels in which each pixel represents or corresponds to a light intensity from the microarray. More specifically, the features of the microarray may provide light emissions that are detected by a corresponding image sensor. In particular embodiments, the features are fluorescently-labeled such that the features provide light emissions when excited by an excitation light. The features of the microarray may have a designated order such that each feature has a known address relative to other features of the microarray.

Figure 19:
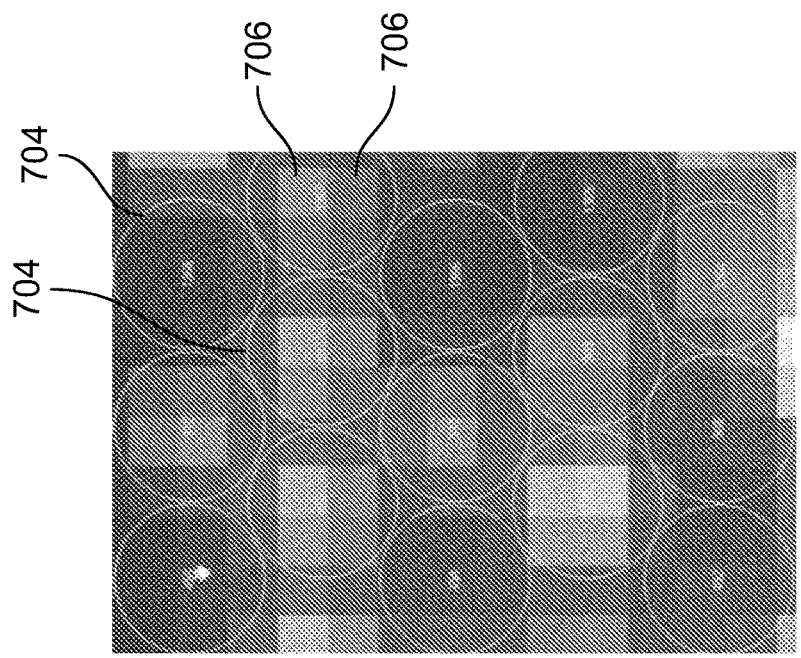
FIG. 19 is an enlarged view of the image of FIG. 18 illustrating feature locators positioned with respect to the microarray.

FIG. 19 is an enlarged view of the image 700 illustrating feature locators 704 of the microarray. Each image may have a known location with respect to the substrate surface that is captured within the image. Each image also has a known area. FIG. 19 also shows individual pixels 706 in which each pixel is a square having a uniform light intensity. After obtaining an image of the microarray, the stitching operation may include identifying a location of the features within the image. In FIG. 19, each of the feature locators 704 is represented by a circle. It is noted that the feature locators 704 are not part of the image 700. Moreover, the stitching operation does not require positioning feature locators 704 with respect to the image. Instead, each of the feature locators 704 represents an identified or determined location of a corresponding feature within the microarray that is shown within the image 700. The feature locators 704 (or locations of the features) may be determined by analyzing the image 700. More specifically, the features (e.g., beads) have a known size and shape and a known order or arrangement with respect to one another within the microarray. For example, in the illustrated embodiment, the features are beads that are arranged in a hexagonal array. With the arrangement and size and shape of the features known, the light intensities of the pixels may be analyzed to determine the positions of the feature locators 704 or, more specifically, the features within the image 700.

The stitching operation may also include determining a signal value for each of the features in the microarray. The signal value for each feature may be based on the light intensities of the pixels that correspond to the feature locator 704 of the corresponding feature. In the illustrated embodiment, each of the features may correspond to a plurality of pixels. For example, the feature locator 704' encircles two complete pixels and eleven portions of other pixels. Some of the other pixels are mostly within the feature locator 704' while some of the other pixels are not mostly within the feature locator 704'. The stitching operation may, for example, determine the signal value by summing the light intensities of the complete pixels and fractions of the light intensities of the other pixels. The fractions may be based on the amount of the corresponding pixel that is within the feature locator 704'. In other words, pixels that are only partially within the feature locator may be weighted. Although one method of determining the signal value is described herein, it should be understood that a number of other formulas exist for determining a signal value that is based on the light intensities of the pixels associated with a particular feature.

The series of images captured by the optical system may include overlapping portions of the microarray. More specifically, the assay protocol may be configured to capture overlapping images to enable stitching the overlapping images together in subsequent analysis. In particular, the overlapping portion within two adjacent images may be used to align or stitch the adjacent images. In some embodiments, the stitching operation includes stitching the images to each other to generate a larger image that includes an entirety of the microarray or a portion of the microarray, such as one section or one feature stripe. However, in an exemplary embodiment, such as the embodiment described with respect to FIGS. 20 and 21, the stitching operation stitches (i.e., combines) data representations of the portions of the microarray that are captured within the images. Stitching data representations together may be less computationally intensive than stitching images of the microarray.

Figure 20:
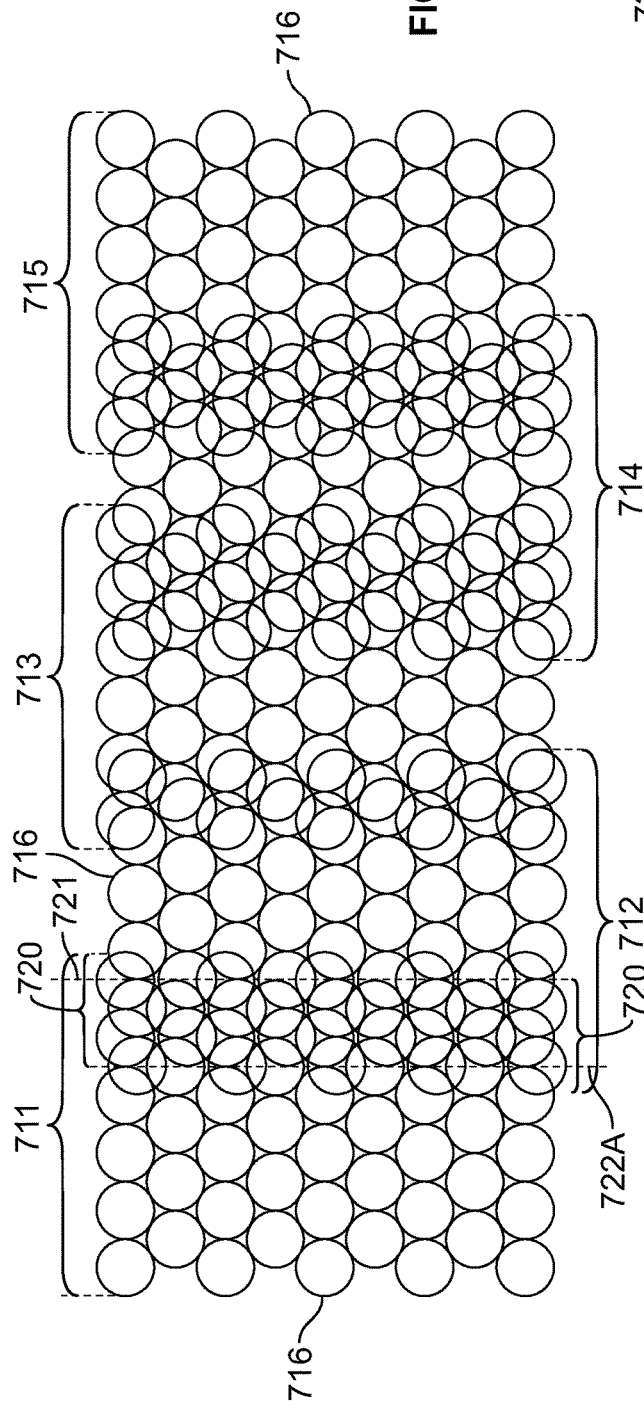
FIG. 20 illustrates a series of overlapping data representations in accordance with an embodiment.
Figure 21:
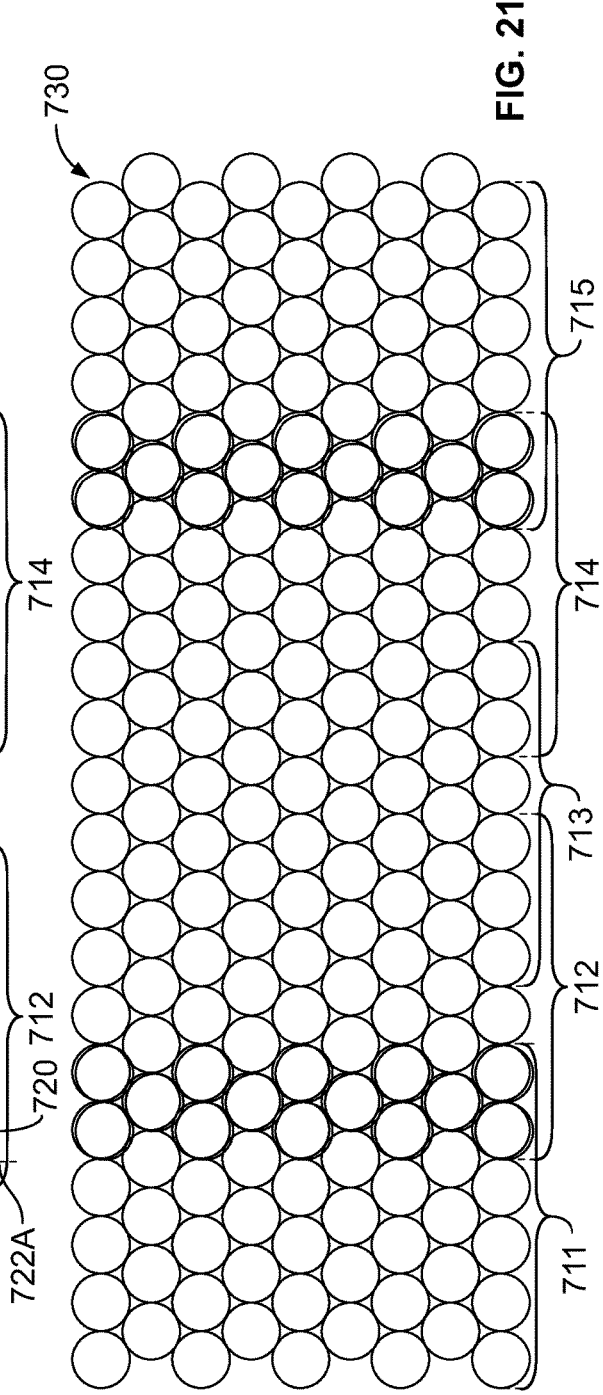
FIG. 21 illustrates the series of overlapping data representations of FIG. 20 after the data representations have undergone a stitching operation in accordance with an embodiment.

FIGS. 20 and 21 schematically demonstrate the stitching operation with respect to a series of data representations. Each data representation corresponds to one of the images captured by the optical system. The stitching operation may stitch (or combine) a plurality of data representations 711-715. Each data representation includes a sub-array of data features 716. Each data feature 716 corresponds to one of the features of the microarray. In FIG. 16, each data feature 716 has a location relative to other data features 716 within the same data representation or sub-array. For example, each location may be represented by an address having a column number and a row number. In other embodiments, each address may be an X, Y coordinate. Although not shown, each data feature 716 may have a signal value assigned thereto that is based on the light intensities associated with the corresponding feature of the microarray. Each of the data representations 711-715 may be generated by identifying the locations of the features and determining the signal value of the corresponding feature as described above. The microarray may have a known pattern or arrangement such that each of the data features 716 may have a known location with respect to other data features.

As shown in FIG. 20, each of the data representations 711-715 may include data features 716 that correspond to features of the microarray that are also represented by data features 716 of an adjacent data representation. In other words, the images represented by the data representations 711-715 overlap each other. The data features 716 that are represented by more than one data representation are located within an overlapping portion 720. Due to tolerances of the assay system, however, the amount of overlap between two adjacent images is not known. Embodiments set forth herein are configured to compare the signal values of the data features 716 within adjacent data representations to identify the data features 716 and combine the data representations together.

In some embodiments, the stitching operation may include comparing one or more columns of the data features 716 of a first data representation to one or more columns of data features 716 of an adjacent second data representation. More specifically, the signal values of one or more columns of data features 716 of the first data representation may be compared to the signal values of one or more columns of data features 716 of the second data representation. Optionally, prior to comparing the signal values, the signal values may be normalized.

As one example, the data representation 711 has a column 721 of data features 716. The column 721 is the right-most column of the data representation 711. The data representation 712 has a column 722A of data features 716. The column 722A is the left-most column of the data representation 712. Embodiments may calculate a correlation value using the signal values of the data features 716 of the column 721 and the signal values of the data features 716 of the column 722A. If the correlation value satisfies a designated threshold, the columns 721, 722A may be designated as overlapping columns that represent the same features of the microarray. If the correlation value does not satisfy the designated threshold, the stitching operation may compare the column 721 to another column of the data representation 712.

In particular embodiments, the stitching operation may compare more than one column of the data representation 711 to more than one column of the data representation 712. Again, a correlation value may be determined. If the correlation value satisfies the designated threshold, the multiple columns of the data representations 711, 712 are designated as overlapping columns that represent the same features of the microarray. If the correlation value does not satisfy the designated threshold, the stitching operation may compare more columns of each of the data representations 711, 712. The designated threshold may be, for example, 60% or more.

The comparing operation may be repeated for each pair of adjacent data representations. For example, in the illustrated embodiment, the comparing operation is also executed between the data representation 712 and 713, between the data representations 713 and 714, and between the data representations 714 and 715. As such, the data representations may be stitched to one another to form a complete representation of the microarray (or of a portion of the microarray, such as one feature stripe). A complete representation 730 formed from the stitched data representations 711-715 is shown in FIG. 21. As shown, data representations that are between two data representations are subjected to two comparing operations. Data representations that are at ends of the microarray are only subjected to one comparing operation.

When stitched to each other, the data representations may combine to provide a complete representation of the microarray (or a discrete portion of the microarray, such as a section or feature stripe). The stitching operation may include comparing the number of features within the complete representation to an expected number of features (e.g., the known number of features in the microarray). If the number of features within the complete representation is equal to the number of expected features in the microarray, the assay system may analyze the features to determine properties or characteristics of the sample.

The complete representation may include absolute coordinates for each feature and a signal value for each feature. Accordingly, the stitching operation may enable determining the location of one feature in a first image relative to the location of another feature that is located in an image that is not adjacent to the first image. By knowing the locations of each feature within the microarray, the chemical substance that is immobilized at the feature may be identified and the signal value of the feature may be used to determine a property or characteristic of a sample. In particular embodiments, the microarray may be used for genotyping.

Although FIGS. 20 and 21 only illustrate five overlapping data representations, it should be understood that embodiments may analyze fewer or more data representations. For example, in some embodiments, the assay system may capture 13 images for each feature stripe of the microarray. The 13 images may be stitched together through the stitching operation. In some embodiments, the number of columns within an overlapping portion between two adjacent data representation may be about 1% of the columns to about 20% of the columns within each data representation. For example, if each data representation included 400 columns of data features, the overlapping portion may include 4 columns to about 80 columns. In particular embodiments, the number of columns within an overlapping portion may be about 2% of the columns to about 15% of the columns within each data representation.

Figure 22:
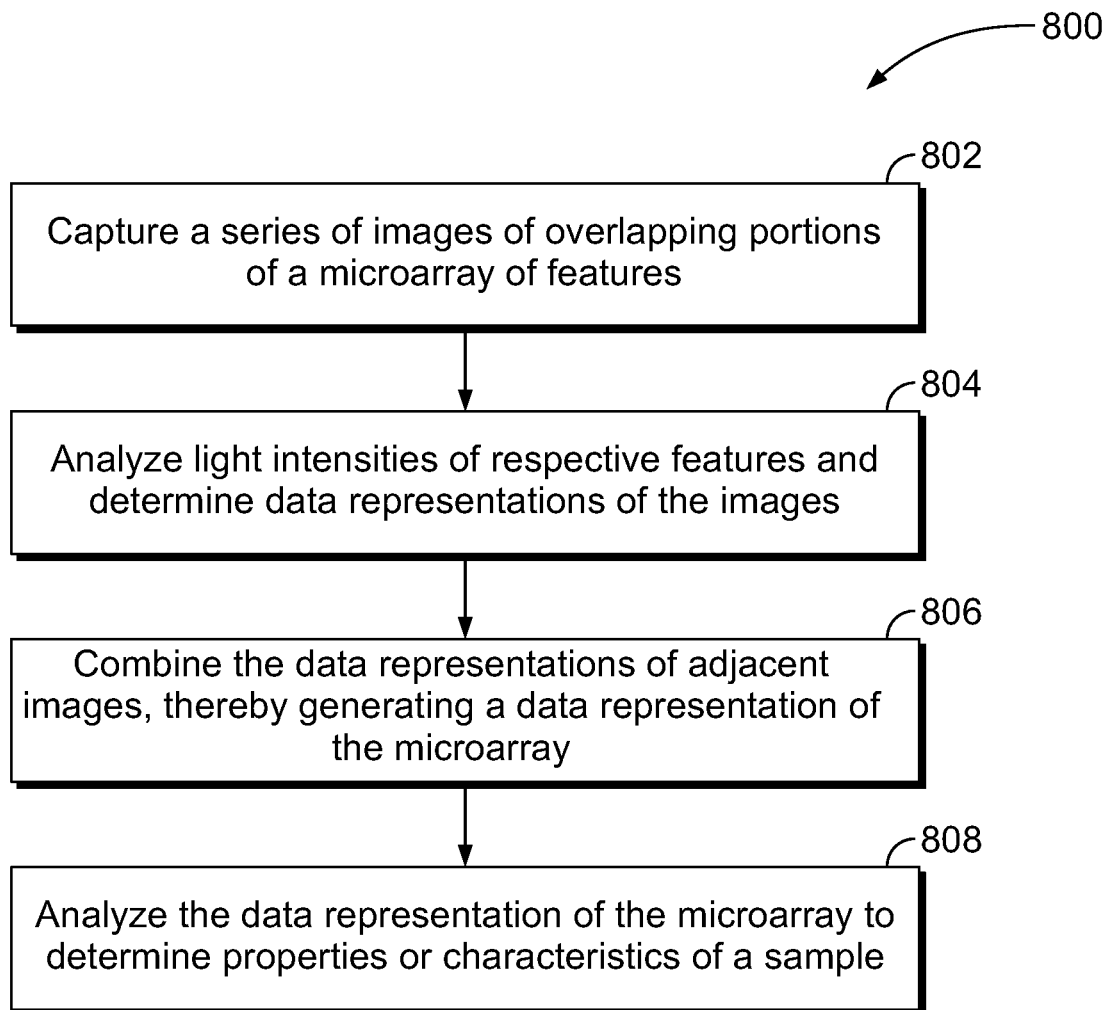
FIG. 22 is a flow-chart illustrating a method in accordance with an embodiment.

As shown in FIG. 22, a method 800 is provided that includes capturing, at 802, a series of images of overlapping portions of a microarray of features. Each of the features has designated probe molecules immobilized thereto. The microarray has target analytes attached thereto. The method 800 also includes analyzing, at 804, light intensities associated with respective features in the images and determine data representations of the images. The data representations have respective sub-arrays of data features that are based on respective features of the microarray. Each of the data features has a corresponding location relative to other data features and a signal value that is based on one or more of the light intensities. The method 800 also includes combining, at 806, the data representations of adjacent images based on a comparison of the signal values of the data features of the data representations of the adjacent images, thereby generating a data representation of the microarray.

The method also includes analyzing, at 808, the data representation of the microarray to determine properties or characteristics of a sample.

In an embodiment, a method is provided that includes positioning a first carrier assembly on a system stage. The first carrier assembly includes a support frame having an inner frame edge that defines a window of the support frame. The first carrier assembly includes a removable first substrate that is positioned within the window and surrounded by the inner frame edge. The first substrate has a sample thereon that is positioned within an imaging zone of an optical system. The method also includes detecting optical signals from the sample of the first substrate using the optical system in accordance with a first imaging protocol. The method also includes replacing the first carrier assembly with a second carrier assembly on the system stage. The second carrier assembly has a removable second substrate. The second substrate has a sample thereon that is positioned within the imaging zone of the optical system, wherein the first and second substrates are different types of substrates. The method also includes detecting optical signals from the sample of the second substrate using the optical system in accordance with a second imaging protocol that is different from the first imaging protocol. Optionally, the first imaging protocol and/or the second imaging protocol are automated.

In one aspect, each of the first and second carrier assemblies includes apertures that extend into the respective carrier assembly. The apertures receive corresponding datums of the system stage when the respective carrier assembly is positioned on the system stage. The second carrier assembly includes an adapter plate that holds the second substrate. The datums engage the first substrate when the first carrier assembly is positioned on the system stage and engaging the adapter plate when the second carrier assembly is positioned on the system stage.

In another aspect, the optical system includes an objective lens, wherein detecting the optical signals from the first substrate includes moving the objective lens and the first substrate relative to each other and wherein detecting the optical signals from the second substrate includes moving the objective lens and the second substrate relative to each other. The optical system detects the optical signals from the first substrate along a first imaging zone. The optical system detects the optical signals from the second substrate along a second imaging zone. The first and second imaging zones are sized differently, wherein the first and second imaging protocols include automatically moving the objective lens relative to the first and second substrates, respectively, along different paths.

In another aspect, the second carrier assembly includes a holding mechanism that includes a movable datum block. The method also includes pressing the datum block, positioning the second substrate on the second carrier assembly, and releasing the datum block. The datum block engages the second substrate to hold the second substrate on the second carrier assembly, wherein the datum block does not hold the first substrate with respect to the first carrier assembly.

In another aspect, the first and second substrates have different thicknesses and first and second substrate surfaces, respectively, wherein detecting optical signals from the first and second substrates includes detecting optical signals from the first and second substrate surfaces, respectively. The first and second substrate surfaces reside along a common plane or being offset by 100 microns or less.

In another aspect, the second substrate includes a microarray of features and detecting optical signals from the second substrate includes capturing a series of images of overlapping portions of the microarray of features. Each of the features has designated probe molecules immobilized thereto. The microarray has target analytes attached thereto. The method also includes analyzing light intensities associated with respective features in the images and determining data representations of the images. The data representations have respective sub-arrays of data features that are based on respective features of the microarray. Each of the data features has a corresponding location relative to other data features and a signal value that is based on one or more of the light intensities. The method also includes combining the data representations of adjacent images based on a comparison of the signal values of the data features of the data representations of the adjacent images, thereby generating a data representation of the microarray. The method also includes analyzing the data representation of the microarray to determine properties or characteristics of a sample.

In another aspect, the first substrate is a flow cell. Optionally, the flow cell includes a flow channel that extends between inlet and outlet ports of the flow cell. The inlet and outlet ports are fluidically coupled to a manifold for flowing a liquid through the flow channel. Optionally, the flow cell includes a plurality of flow channels that extend between respective inlet and outlet ports of the flow cell. The inlet and outlet ports are fluidically coupled to a manifold for flowing a liquid through the flow channel.

In another aspect, the method also includes iteratively flowing reagents through the flow cell to conduct a sequencing-by-synthesis (SBS) protocol.

In another aspect, the first and second imaging protocols include moving an objective lens and/or the system stage relative to each other along different paths.

In another aspect, the second substrate is an open-face substrate having biological or chemical substances immobilized to an exterior surface of the open-face substrate. Optionally, the open-face substrate includes a microarray along the exterior surface. Optionally, the microarray includes a plurality of feature stripes that extend parallel to each other. Each of the feature stripes has an array of reaction sites.

In another aspect, each of the first and second carrier assemblies includes apertures that extend into the respective carrier assembly. The apertures receive corresponding datums when the respective carrier assembly is positioned on the system stage. Optionally, the first substrate engages the datums and the second substrate does not engage the datums.

In another aspect, the first substrate is larger than the second substrate.

In another aspect, the optical system includes an objective lens. The step of detecting the optical signals from the first substrate includes moving the objective lens and the first substrate relative to each other. The step of detecting the optical signals from the second substrate includes moving the objective lens and the second substrate relative to each other.

In another aspect, the optical system detects the optical signals from the first substrate along a first imaging zone. The optical system detects the optical signals from the second substrate along a second imaging zone. The first and second imaging zones are sized differently.

In another aspect, the first and second imaging protocols include automatically moving the objective lens relative to the first and second substrates, respectively, along different paths.

In another aspect, the first and second carrier assemblies engage the system stage in effectively identical manners.

In an embodiment, a method is provided that includes positioning a first carrier assembly on a system stage. The first carrier assembly includes a support frame having an inner frame edge that defines a window of the support frame. The first carrier assembly includes a first substrate that is positioned within the window and surrounded by the inner frame edge. The first substrate has a sample thereon that is positioned within an imaging zone of an optical system. The method also includes detecting optical signals from the sample of the first substrate using the optical system and replacing the first carrier assembly with a second carrier assembly on the system stage. The second carrier assembly includes a support frame and an adapter plate that is coupled to the support frame. The second carrier assembly has a second substrate that is held by the adapter plate that has a sample thereon. The sample of the second substrate is positioned within the imaging zone of an optical system. The method also includes detecting optical signals from the sample of the second substrate using the optical system.

In another aspect, the first substrate is a flow cell. Optionally, the flow cell includes a flow channel that extends between inlet and outlet ports of the flow cell. The inlet and outlet ports are fluidically coupled to a manifold for flowing a liquid through the flow channel. Optionally, the flow cell includes a plurality of flow channels that extend between respective inlet and outlet ports of the flow cell. The inlet and outlet ports are fluidically coupled to a manifold for flowing a liquid through the flow channel. Optionally, the flow channels extend parallel to each other through the imaging zone.

In another aspect, the method includes iteratively flowing reagents through the flow cell to conduct a sequencing-by-synthesis (SBS) protocol.

In another aspect, the second substrate is an open-face substrate having biological or chemical substances immobilized to an exterior surface of the open-face substrate. Optionally, the open-face substrate includes a microarray along the exterior surface.

In another aspect, the first substrate is larger than the second substrate.

In another aspect, the support frame of the first carrier assembly and the support frame of the second carrier assembly are the same support frame.

In another aspect, the support frame of the first carrier assembly and the support frame of the second carrier assembly are different support frames that have respective outer edges that define identical perimeters.

In another aspect, the first substrate is slidable within the window along an XY-plane that extends parallel to the inner frame edge and wherein the adapter plate is slidable within the window along the XY-plane.

In another aspect, the system stage includes a plurality of datums. The datums engage the first substrate and engage the adapter plate during the positioning and replacing operations.

In another aspect, the adapter plate includes an inner plate edge that defines a pocket. The second substrate is disposed within the pocket and engages the plate edge.

In another aspect, the optical system includes an objective lens. The step of detecting the optical signals from the first substrate includes moving the objective lens and the first substrate relative to each other. The step of detecting the optical signals from the second substrate includes moving the objective lens and the second substrate relative to each other.

In another aspect, the optical system detects the optical signals from the first substrate along a first imaging zone. The optical system detects the optical signals from the second substrate along a second imaging zone. The first and second imaging zones are sized differently.

In another aspect, the samples of the first and second substrates are positioned within different sections of the window.

In another aspect, the step of replacing the first carrier assembly with the second carrier assembly includes removing the first substrate from the support frame and positioning the second substrate within the adapter plate.

In another aspect, the second carrier assembly includes a holding mechanism that includes a movable datum block that is disposed within a portion of the pocket. The method includes pressing the datum block, positioning the second substrate within the pocket, and releasing the datum block. The datum block engages the second substrate to hold the second substrate in the pocket. Optionally, the holding mechanism includes a biasing spring that provides a resilient force for holding the second substrate within the pocket.

In an embodiment, a carrier assembly is provided that includes a support frame having an inner frame edge that defines a window of the support frame. The carrier assembly also includes an adapter plate that is coupled to the support frame and positioned within the window. The adapter plate includes a plate body having an inner plate edge that defines a pocket for receiving a substrate that is sized smaller than the window. The inner plate edge also defines a holding recess that opens to the pocket. The carrier assembly also includes a movable datum block positioned within the holding recess. The datum block is movable between a retracted position and an engaged position. The datum block is configured to engage the substrate when the datum block is in the engaged position and press the substrate against an opposing surface of the adapter plate to hold the substrate within the pocket.

In one aspect, the adapter plate extends parallel to an XY plane and faces in a direction along a Z axis. The datum block provides a holding force that is directed along the XY plane.

In another aspect, the pocket at least one of coincides with a receiving plane that intersects the inner frame edge or is positioned below the receiving plane.

In another aspect, the inner frame edge defines apertures that open to the window. The apertures are configured for receiving datums when the carrier assembly is positioned on a system stage. Optionally, the support frame includes first and second body sides. The first body side is configured to face an objective lens during an imaging operation and the second body side is configured to be positioned on a base surface during the imaging operation. The apertures of the support frame open to the second body side and extend from the second body side toward the first body side.

In another aspect, the adapter plate is slidable along an XY plane within the window.

In another aspect, the adapter plate includes openings that open to the pocket.

In another aspect, the pocket is sized and shaped to receive a planar chip or slide.

In an embodiment, a carrier assembly is provided that includes a support frame having an inner frame edge that defines a window of the support frame. The carrier assembly also includes an adapter plate that is coupled to the support frame and positioned within the window. The inner frame edge defines a substrate-receiving recess positioned above the adapter plate. The substrate-receiving recess is configured to receive a first planar substrate. The adapter plate includes a plate body having an inner plate edge that defines a pocket for receiving a second planar substrate that is sized smaller than the first planar substrate. The pocket exists at least partially below the substrate-receiving recess.

In another aspect, the carrier assembly includes a datum block that is movable between a retracted position and an engaged position. The datum block is configured to engage the substrate when the datum block is in the engaged position and press the substrate against an opposing surface of the adapter plate to hold the substrate within the pocket.

Optionally, the adapter plate extends parallel to an XY plane and faces in a direction along a Z axis. The datum block provides a holding force that is directed along the XY plane.

In another aspect, the inner frame edge defines apertures that open to the window. The apertures are configured for receiving datums when the carrier assembly is positioned on a system stage.

Optionally, the support frame includes first and second body sides. The first body side is configured to face an objective lens during an imaging operation and the second body side is configured to be positioned on a base surface during the imaging operation. The apertures of the support frame open to the second body side and extend from the second body side toward the first body side.

In another aspect, the adapter plate is slidable along an XY plane within the window.

In another aspect, the pocket is sized and shaped to receive a planar chip or slide.

In another aspect, the adapter plate includes fluid openings that provide access to the substrate-receiving recess.

In another aspect, at least one of the fluid openings is located at a first end of the adapter plate and at least one of the fluid openings is located at an opposite second end of the adapter plate.

In one aspect, an assay system is provided that includes a system stage having a base surface that extends parallel to an XY plane and a plurality of datums coupled to the base surface. The datums include projections that extend away from the base surface along a Z axis that is perpendicular to the XY plane. The assay system also includes an optical system including an objective lens. The objective lens is configured to move relative to the system stage along the XY plane. The assay system also includes a fluidic control system configured to control flow of one or more fluids through a flow cell when the flow cell is mounted onto the system stage. The assay system also includes a system controller configured to control the fluidic control system and the optical system to conduct different first and second assay protocols with first and second samples, respectively. During the first assay protocol, the system controller commands the fluidic control system to direct one or more fluids through the flow cell on the system stage and commands the optical system to detect optical signals from the first sample on the flow cell. During the second assay protocol, the system controller commands the optical system to detect optical signals from the second sample on an open-face substrate on the system stage without flowing fluids through the second sample.

In one aspect, the first assay protocol is a sequencing-by-synthesis (SBS) protocol and the second assay protocol includes imaging a microarray.

In another aspect, the assay system also includes a carrier sensor that is configured to detect a type of carrier assembly mounted onto the system stage. The assay system is configured to issue a notification when the carrier assembly and the selected assay protocol do not match.

In another aspect, the assay system includes a carrier assembly having a support frame that defines a window. The support frame is configured to couple to an adapter plate that extends across and covers the window.

In one embodiment, a method is provided that includes capturing a series of images of overlapping portions of a microarray of features. Each of the features has designated probe molecules immobilized thereto. The microarray has target analytes attached thereto. The method also includes analyzing light intensities associated with respective features in the images to determine data representations of the images. The data representations have respective sub-arrays of data features that are based on respective features of the microarray. Each of the data features has a corresponding location relative to other data features and a signal value that is based on one or more of the light intensities. The method also includes combining the data representations of adjacent images based on a comparison of the signal values of the data features of the data representations of the adjacent images, thereby generating a data representation of the microarray. The method also includes analyzing the data representation of the microarray to determine properties or characteristics of a sample.

In one aspect, each of the data representations includes a plurality of columns of the features. The comparison includes comparing the signal values of a column of one data representation to the signal values of a column of the adjacent data representation. The method includes calculating a correlation value based on the comparison. The columns are designated as overlapping columns that have the same features if the correlation value satisfies a designated threshold.

In some aspects, each of the data representations includes a plurality of columns of the features. The comparison includes comparing the signal values of a plurality of the columns of one data representation to the signal values of a plurality of the columns of the adjacent data representation. Optionally, the method includes calculating a correlation value based on the comparison. The columns are designated as overlapping columns that have the same features if the correlation value satisfies a designated threshold.

In some aspects, the combining operation is repeated for each pair of adjacent images, thereby generating the data representation of the microarray.

In some aspects, analyzing the data representation of the microarray is performed after comparing the number of features within the data representation of the microarray to an expected number of features.

In some aspects, the features of the microarray have a known size and shape and a known order or arrangement with respect to one another within the microarray.

In some aspects, each of the features corresponds to a plurality of pixels in the corresponding image.

It is to be understood that the above description is intended to be illustrative, and not restrictive. For example, the above-described embodiments (and/or aspects thereof) may be used in combination with each other. In addition, many modifications may be made to embodiments without departing from the of the scope invention in order to adapt a particular situation or material. While the specific components and processes described herein are intended to define the parameters of the various embodiments, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

What is claimed is:

1. A carrier assembly comprising:
a support frame having an inner frame edge that defines a window of the support frame;
an adapter plate coupled to the support frame and positioned within the window, the adapter plate including a plate body having an inner plate edge that defines a pocket for receiving a substrate that is sized smaller than the window, the inner plate edge also defining a holding recess that opens to the pocket; and
a movable datum block positioned within the holding recess, the datum block being movable between a retracted position and an engaged position, the datum block configured to engage the substrate when the datum block is in the engaged position and press the substrate against an opposing surface of the adapter plate to hold the substrate within the pocket.

2. The carrier assembly of claim 1, wherein the adapter plate extends parallel to an XY plane and faces in a direction along a Z axis, the datum block providing a holding force that is directed along the XY plane.

3. The carrier assembly of claim 1, wherein the pocket at least one of coincides with a receiving plane that intersects the inner frame edge or is positioned below the receiving plane.

4. The carrier assembly of claim 1, wherein the adapter plate is slidable along an XY plane within the window.

5. The carrier assembly of claim 1, wherein the datum block comprises an engagement surface that extends into the pocket and is to engage the substrate.

6. The carrier assembly of claim 1, further comprising: a passage at least partially defined between an edge of the adapter plate and a portion of an edge of the substrate after the substrate is received, wherein the passage is sized and shaped to permit a portion of an individual's digit to be inserted therein and engage the substrate edge for loading or removing the substrate.

7. The carrier assembly of claim 1, wherein the support frame comprises a frame body comprising a plurality of apertures sized and shaped to receive respective datums of a system stage.

8. The carrier assembly of claim 7, wherein one or more of the datums of the system stage is to stop movement of the adapter plate.

9. The carrier assembly of claim 8, wherein one or more of the datums of the system is to stop movement of a second substrate positioned in the window when the adapter plate is removed from the carrier assembly.

10. The carrier assembly of claim 1, wherein the plate body of the adapter plate comprises a substrate platform within the pocket to have the substrate positioned thereon.

11. The carrier assembly of claim 10, wherein the plate body of the adapter plate comprises a recess that surrounds the substrate platform.

12. A carrier assembly comprising:
a support frame having an inner frame edge that defines a window of the support frame; and
an adapter plate removably coupled to the support frame and positioned within the window, the inner frame edge defining a substrate-receiving recess positioned above the adapter plate, the substrate-receiving recess being configured to receive a first planar substrate, the adapter plate including a plate body having an inner plate edge that defines a pocket for receiving a second planar substrate that is sized smaller than the first planar substrate, the pocket existing at least partially below the substrate-receiving recess.

13. The carrier assembly of claim 1, wherein the adapter plate is removably coupled to the support frame.

14. The carrier assembly of claim 13, wherein when the adapter plate is removed, the window is to receive a second substrate larger than the substrate received in the pocket.

15. The carrier assembly of claim 14, wherein the inner frame edge is to engage an edge of the second substrate.

16. The carrier assembly of claim 14, wherein the substrate received in the pocket comprises a microarray comprising a plurality of array sections, each of the array sections comprising a plurality of stripes.

17. The carrier assembly of claim 16, wherein the second substrate is a flow cell.

18. The carrier assembly of claim 12, wherein the first planar substrate comprises a microarray and wherein the second planar substrate comprises a flow cell.

19. The carrier assembly of claim 12, wherein the inner frame edge defines apertures that are sized and shape to receive datums for aligning the second planar substrate.

20. A carrier assembly system, comprising:
a carrier assembly comprising:
a support frame having an inner frame edge that defines a window of the support frame;
an adapter plate configured to be removably coupled to the support frame and positioned within the window, the adapter plate comprising a plate body having an inner plate edge that defines a pocket for receiving a first substrate that is sized smaller than the window;
the first substrate; and
a second substrate that is sized larger than the first substrate, wherein the window is configured to receive the second substrate when the adapter plate is not coupled to the support frame.

* * * * *